US009492398B2

(12) United States Patent
Rossines et al.

(10) Patent No.: US 9,492,398 B2
(45) Date of Patent: Nov. 15, 2016

(54) NANOCAPSULATION OF ESSENTIAL OILS FOR PREVENTING OR CURING INFECTIOUS DISEASES ALONE OR WITH AN ANTIBIOTIC

(75) Inventors: Elisabeth Rossines, Avesse (FR); Marie Laure Joly-Guillou, Angers (FR); Patrick Saulnier, Marigne (FR); Jean Pierre Benoit, Angers (FR)

(73) Assignees: Eydo Pharma, Romorantin Lanthenay (FR); Institut National de la Sante et de la Recherche Medicale, Paris (FR); Université d'Angers, Anders (FR)

( * ) Notice: Subject to any disclaimer, the term of this patent is extended or adjusted under 35 U.S.C. 154(b) by 291 days.

(21) Appl. No.: 13/985,686

(22) PCT Filed: Feb. 24, 2012

(86) PCT No.: PCT/IB2012/000663
§ 371 (c)(1),
(2), (4) Date: Oct. 29, 2013

(87) PCT Pub. No.: WO2012/114201
PCT Pub. Date: Aug. 30, 2012

(65) Prior Publication Data
US 2014/0045692 A1    Feb. 13, 2014

Related U.S. Application Data

(60) Provisional application No. 61/446,719, filed on Feb. 25, 2011.

(51) Int. Cl.
| | |
|---|---|
| *A61K 9/51* | (2006.01) |
| *A61K 9/107* | (2006.01) |
| *A61K 31/015* | (2006.01) |
| *A61K 31/05* | (2006.01) |
| *A61K 31/085* | (2006.01) |
| *A61K 31/11* | (2006.01) |
| *A61K 31/35* | (2006.01) |
| *A61K 31/407* | (2006.01) |
| *A61K 31/424* | (2006.01) |
| *A61K 31/43* | (2006.01) |
| *A61K 31/431* | (2006.01) |
| *A61K 31/4412* | (2006.01) |
| *A61K 31/47* | (2006.01) |
| *A61K 31/496* | (2006.01) |
| *A61K 31/664* | (2006.01) |
| *A61K 31/733* | (2006.01) |
| *A61K 45/06* | (2006.01) |
| *A61K 36/15* | (2006.01) |
| *A61K 36/53* | (2006.01) |
| *A61K 36/54* | (2006.01) |
| *A61K 36/61* | (2006.01) |
| *A01N 65/00* | (2009.01) |
| *A01N 25/28* | (2006.01) |
| *A01N 65/22* | (2009.01) |

(Continued)

(52) U.S. Cl.
CPC ............... *A61K 9/51* (2013.01); *A01N 25/28* (2013.01); *A01N 65/00* (2013.01); *A01N 65/22* (2013.01); *A01N 65/24* (2013.01); *A01N 65/28* (2013.01); *A61K 9/1075* (2013.01); *A61K 9/5123* (2013.01); *A61K 9/5146* (2013.01); *A61K 31/015* (2013.01); *A61K 31/05* (2013.01); *A61K 31/085* (2013.01); *A61K 31/11* (2013.01); *A61K 31/35* (2013.01); *A61K 31/407* (2013.01); *A61K 31/424* (2013.01); *A61K 31/43* (2013.01); *A61K 31/431* (2013.01); *A61K 31/4412* (2013.01); *A61K 31/47* (2013.01); *A61K 31/496* (2013.01); *A61K 31/664* (2013.01); *A61K 31/733* (2013.01); *A61K 36/15* (2013.01); *A61K 36/53* (2013.01); *A61K 36/54* (2013.01); *A61K 36/61* (2013.01); *A61K 45/06* (2013.01)

(58) Field of Classification Search
CPC ...... A61K 2300/00; A61K 8/97; A61K 9/51; A61K 9/5146
See application file for complete search history.

(56) References Cited

U.S. PATENT DOCUMENTS

| | | | |
|---|---|---|---|
| 2003/0022242 A1* | 1/2003 | Anderson | A61K 9/1274 435/7.1 |
| 2004/0071757 A1* | 4/2004 | Rolf | A61K 9/007 424/443 |

(Continued)

FOREIGN PATENT DOCUMENTS

| | | | | |
|---|---|---|---|---|
| JP | 08-020510 | 1/1996 | ............ | A01N 65/00 |
| JP | 2002-519152 | 7/2002 | ............... | A61L 9/14 |

(Continued)

OTHER PUBLICATIONS

International Search Report and Written Opinion for International Application No. PCT/IB2012/000663, May 22, 2012.

(Continued)

*Primary Examiner* — Johann R Richter
*Assistant Examiner* — Danielle Sullivan
(74) *Attorney, Agent, or Firm* — Kunser & Jaffe

(57) ABSTRACT

A composition, an encapsulated composition and/or nanoparticles comprising at least one essential oil having a large spectrum antibacterial, antiparasitic, antifungal activity and/or a plant antipathogen, optionally at least one antibiotic and optionally a pharmaceutically acceptable carrier is disclosed. Methods for treating infectious diseases and especially bacterial, parasitic, fungal and/or plant infectious by using this composition, encapsulated composition and/or nanoparticles are also disclosed.

11 Claims, 19 Drawing Sheets

(51) Int. Cl.
*A01N 65/24* (2009.01)
*A01N 65/28* (2009.01)

(56) References Cited

U.S. PATENT DOCUMENTS

2010/0233275 A1  9/2010  Saulnier .................... 424/490
2012/0027825 A1  2/2012  Benoit et al. ................ 424/401

FOREIGN PATENT DOCUMENTS

| JP | 2003-113013 | 4/2003 | ............ A01N 65/00 |
| WO | WO 00/01423 | 1/2000 | ............ A61L 9/14 |
| WO | WO 2008/155592 | 12/2008 | ............ A61K 9/127 |
| WO | WO 2009/004214 | 1/2009 | ............ A61K 9/51 |
| WO | WO 2009/029046 | 3/2009 | ............ A61K 8/00 |
| WO | WO 2009/043987 | 4/2009 | ............ A61K 36/00 |
| WO | WO 2009/132050 | 10/2009 | ........... A61K 39/395 |
| WO | WO 2010/067037 | 6/2010 | ............ B01J 13/04 |

OTHER PUBLICATIONS

Sung et al., "Activity of essential oil from Mentha piperita against some antibiotic-resistant *Streptococcus pneumonia* strains and its combination effects with antibiotics," Natural Product Sciences, Korean Society of Pharmacognosy, Seoul, Korea, vol. 13, No. 2, pp. 164-168, Jan. 1, 2007.

Detoni et al., "Essential oil from Zanthoxylum tingoassuiba loaded into multilamellar lipsomes useful as antimicrobial agents," Journal of Microencapsulation 2009 Informa Healthcare Gbr Lnkd, vol. 26, No. 8, pp. 684-691, Dec. 2009.

Valenti et al., "Liposome-incorporated Santolina insularis essential oil: Preparation characterization and in vitro antiviral activity," Journal of Liposome Research, Taylor & Francis, Philadelphia, Pennsylvania, vol. 11, No. 1, pp. 73-90, Jan. 1, 2001.

\* cited by examiner

NANOCAPSULATION OF ESSENTIAL OILS FOR PREVENTING OR CURING INFECTIOUS DISEASES ALONE OR WITH AN ANTIBIOTIC

RELATED APPLICATIONS

The present application is a U.S. National Stage Application of International Application No. PCT/IB2012/000663, filed Feb. 24, 2012, which claims priority from U.S. Provisional Application Ser. No. 61/446,719, filed Feb. 25, 2011, said patent applications hereby fully incorporated herein by reference

FIELD OF THE INVENTION

The present invention relates to compositions, an encapsulated composition and/or nanoparticles comprising at least one essential oil or at least one essential oil extract having a large spectrum antibacterial activity, optionally at least one antibiotic associated with the essential oil or encapsulated with the essential oil or at least one essential oil extract in nanocapsules or nanoparticles and optionally a pharmaceutically acceptable carrier. Methods for treating bacterial infections, parasitic infections, fungal infections, undesirable vegetation or weeds and/or plant pathogens by using compositions, encapsulated compositions and/or nanoparticles containing at least one essential oil or at least one essential oil extract are also disclosed.

BACKGROUND OF THE INVENTION

Nosocomial infections are those infections that are acquired during hospitalization of a patient or any health care-associated infection including infections acquired in institutions other than acute care facilities such as nursing homes. They are infections that are newly acquired and are identified at least forty-eight hours after admission, so that infections acquired prior to entry into a health care facility are in fact excluded from the definition of nosocomial.

The most common nosocomial infections are urinary tract infections, surgical site infections, pneumonia and primary blood stream infections caused by central vascular line infections, which later is caused by the use of indwelling central vascular catheters.

6.9% of patients admitted to French hospitals, 8 to 10% of patients admitted to hospitals in Europe, other than in France and 10% of patients admitted to hospitals in the United States are stricken with at least one nosocomial infection during their stay. This results in about 4,200 deaths in France, 50,000 deaths in Europe and 99,000 deaths in the United States per year. Moreover, patients have to postpone their hospitalization anywhere from 4 to 24 days depending on the type of nosocomial infection.

Nosocomial infections are quite costly. The direct costs of hospital-acquired infections in the United States are estimated to be about $4.5 billion dollars per year. In England the cost for one health care unit is estimated to be about 3.6 million pounds per year.

The over consumption of antibiotics and in particular the antibacterial drugs are the principle cause of nosocomial infections. The constant utilization of antibiotics, and in particularly in hospitals, creates a pressure selection that favors bacteria that are resistant to certain antibiotics and contributes to bacterial strains that are multi resistant that can be transmitted from one patient to another. This phenomenon, in some instances, prevents treatment with antibiotics that were initially used to successfully treat bacterial infections. It is also known that within the next several years many antibiotics will become ineffective to treat bacterial infections due to bacterial resistance. In addition, the pharmaceutical industry placed only a few new antibiotics on the market for the last ten years.

Cell communication in bacteria, parasites and fungus occurs in a population density dependent manner and is based on the production of and response to small pheromone-like molecules called autoinducers. This form of intercellular signalling is known as quorum sensing, which is a means to communicate between the same species that optimizes the metabolic and behavorial activity. Quorum sensing regulated genes encode not only virulence factors, but also other proteins involved in the metabolic process.

The lipophilic nature of essential oils is a major drawback for their biodisperability in a hydrophilic medium. However, membranes of microorganisms possess lipophilic sites where the essential oils are in a favourable interactional environment. Films can form on the surface of the microorganisms and act as a vector for the reduction of the capacity of the microorganisms to communicate between themselves. This by consequence reduces the microorganism's capacity to form biofilms.

Traditionally quorum sensing was thought to help microorganisms to coordinate processes such as biofilm formation that would be inefficient in single cells or to prevent too many microorganisms from colonizing in too small an area. However recently it has been discovered that quorum seeking exists in single cells which are confined in an extremely enclosed space.

Essential oils are aromatic volatile concentrated hydrophobic liquids that can be found in different parts of plants such as the seeds, the roots, the bark, the wood, leaves, shoots or peel. They are generally produced and stored in the secretory cells, the gland and resinous ducts of plants. They can be obtained from plants by various processes including by compression, distillation, extraction, absorption or by applying pressure and maceration.

Essential oils can be used in many applications such as antiparasitics, insecticides, fungicides, in medicaments and in compositions for cosmetics. Essential oils are effective as anti-bacterials due to a synergistic combined action of various components on the bacterial cell wall, cell membrane metabolism and protein synthesis.

For instance WO2009/043987 describes a composition that contains an antibiotic and at least one essential oil that are used as anti-infectious agents and especially as anti-bacterials. In vivo and in vitro applications of their effectiveness are demonstrated in this patent application for a variety of bacterial infections.

There are three types of submicroscopic vectors allowing the transport of active principles which are liposomes, nanocapsules, nanospheres and nano-emulsions.

Liposomes are microscopic vesicles, generally spherically shaped, formed from one or more lipid walls. The walls are prepared from lipid molecules, which have the tendency both to form bilayers and to minimize their surface area. The lipid molecules that make up a liposome have hydrophilic and lipophilic portions. Upon exposure to water, the lipid molecules form one or several bilayer membranes wherein the lipid ends of the molecules in each layer are directed to the center of the membrane, and the opposing polar ends form the respective inner and outer surfaces of the bilayer membrane. Thus, each side of the membrane presents a hydrophilic surface while the interior of the membrane comprises a lipophilic medium.

Nanospheres are matrix type structures consisting of solid spheres, in which the active principle is trapped or dissolved.

Nanocapsules are vesicles comprising an envelope which is generally of macromolecular nature and the active principle is likely to be contained in the core limited by the envelope in the shell or adsorbed on the envelope of the vesicles.

Nanoemulsions are dispersions of very small droplets such as oil in water or water in oil having a size in the range of 10 nm to 200 nm. They are often formulated using high energy methods such as ultrasound or high pressure homogenizations that promote a very fine fractioning of emulsionated systems. Nanoemulsions can also be obtained using low energy methods such as spontaneous emulsification or phase inversion temperature.

Liposomes have some important drawbacks in drug deliver since they have a low capacity to encapsulate lipophilic drugs, are manufactured through a process that involves organic solvents, which represent potential toxicity for human use and they are leaky and unstable in biological fluids and more generally in aqueous solutions.

Nanospheres, many of which are obtained by the process of salting out, also have such problems such as the use of large quantities of acetone and salts, a long purification process, possible incompatibility between the salt use in the process and the active principle and the use of large quantities of residual polyvinylic alcohol, which is not suitable for all types of administration.

Nanocapsules and nanoemulsions also present obstacles in their preparation since large quantities of surfactants and cosurfactants are used, which can present a potential toxicity for human use. Furthermore, their formulation can involve high energy methods that can alter the chemical and biological activity of the encapsulated active principles. When formulated with low energy methods, the related suspensions suffer from kinetic instability mainly in relation with the Ostwald ripening.

EP 1 265 698 B1 describes lipid nanocapsules that have a lipid core that is liquid or semisolid at room temperature, a method for preparing these nanocapsules and their use as a medicine.

WO2009/004214 A2 describes a process of preparing nanocapsules which has the active principle encapsulated in the interior of the capsule and which is prepared by a phase-inversion temperature method.

There is a need in the art to provide essential oils or essential oil extracts that can be used for treating infections, undesirable vegetation or weeds and/or plant pathogens and more specifically bacterial infections, parasitic infections, fungal infections, undesirable vegetation or weeds and/or plant pathogens in which the essential oils or essential oil extracts are formulated such that they are more medicinally effective or effective when used in smaller amounts. There is also a need in this art to provide a delivery systems for essential oils or essential oil extracts that produce a synergistic effect.

Yet another object of the present invention is to provide a process for reducing and/or limiting and/or retarding the virulence of pathogens by enveloping the pathogens of bacteria, parasites, fungus, undesirable vegetation or weeds and/or plant pathogens by quorum sensing.

In yet another object the present invention provides essential oils or essential oil extracts encapsulated in nanocapsules or nanoparticles wherein an outer film is mechanically formed on the nanocapsules, which is in contact with the lipophilic sites of the membranes of the pathogens of bacteria, parasites, fungus, undesirable vegetation or weeds and/or plant pathogens.

This need and other objects are achieved by the present invention as evidenced by the summary of the invention, description of the preferred embodiments and the claims.

SUMMARY OF THE INVENTION

The present invention relates to a composition, an encapsulated composition and/or nanoparticles comprising, consisting essentially of, or consisting of at least one essential oil or at least one essential oil extract having a broad spectrum antibacterial activity, as described herein, antiparasitic activity, antifungal activity, undesirable vegetation activity, weed activity and/or plant pathogenic activity.

The present invention also relates to a composition, an encapsulated composition and/or nanoparticles comprising, consisting essentially of, or consisting of at least one essential oil or at least one essential oil extract having a broad spectrum antibacterial activity, as described herein, antiparasitic activity, antifungal activity, undesirable vegetation activity, weed activity and/or plant pathogenic activity, optionally at least one antibiotic, as described herein, associated with or encapsulated with the at least one essential oil and optionally a pharmaceutically acceptable carrier.

The at least one essential oil or at least one essential oil extract that can be used in the composition, the encapsulated composition and/or the nanoparticles include essential oils or essential oil extracts from oregano, essential oils or essential oil extracts from oregano from Spain or Morocco or the Balkans, essential oils or essential oil extracts from thyme, essential oils or essential oil extracts from cloves, essential oils or essential oil extracts from the leaves of cloves, essential oils or essential oil extracts from savory, essential oils or essential oil extracts from ravintsara, essential oils or essential oil extracts from laurel leaves, essential oils or essential oil extracts from scotch pine, essential oils or essential oil extracts from eucalyptus, essential oils or essential oil extracts from paper bark, essential oils or essential oil extracts from green paper bark, essential oils or essential oil extracts from red thyme, essential oils or essential oil extracts from Sarriette, essential oils or essential oil extracts from Chinese cinnamon and essential oils or essential oil extracts from cinnamon.

In another embodiment the present invention relates to an encapsulated composition comprising, consisting essentially of, or consisting of a composition comprising an essential oil from oregano from Morocco or the Balkans having about 33.20% or 70% of carvacrol (14.7 unit grams of carvacrol), an essential oil from clove leaves or cloves from Madagascar having 82.57% eugenol (70.6 unit grams of eugenol) and essential oil from cinnamon from China having 77.57% of trans cinnamaldehyde (14.7 unit grams of trans cinnamaldehyde).

In yet another embodiment the present invention relates to an encapsulated composition comprising, consisting essentially of, or consisting of a composition having four essential oil extracts, which are about 11.86% carvacrol extract (5.25 unit grams of carvacrol) from oregano, 63.28% eugenol (54.10 unit grams of eugenol) an essential oil extract from clove leaves or cloves from Madagascar, 13.56% of trans cinnamaldehyde extract (2.57 unit grams of trans cinnamaldehyde) an essential oil extract from cinnamon from China and 11.3% trans-β-caryophyllene (1.80 unit grams of trans-β-caryophyllene) from oregano, cloves and/or cinnamon.

In another embodiment the present invention relates to nanoparticles comprising, consisting essentially of, or consisting of a composition comprising an essential oil from oregano from Morocco or the Balkans having about 33.20% or 70% of carvacrol (14.7 unit grams of carvacrol), an essential oil from clove leaves from Madagascar having 82.57% eugenol (70.6 unit grams of eugenol) and essential oil from cinnamon from China having 77.57% of trans cinnamaldehyde (14.7 unit grams of trans cinnamaldehyde).

In yet another embodiment the present invention relates to compositions and/or nanoparticles comprising, consisting essentially of, or consisting of a composition having four essential oil extracts, which are about 11.86% carvacrol extract (5.25 unit grams of carvacrol) from oregano, 63.28% eugenol (54.10 unit grams of eugenol) an essential oil extract from clove leaves or cloves from Madagascar, 13.56% of trans cinnamaldehyde extract (2.57 unit grams of trans cinnamaldehyde) an essential oil extract from cinnamon from China and 11.3% trans-β-caryophyllene (1.80 unit grams of trans-β-caryophyllene) from oregano, cloves and/or cinnamon.

In yet another embodiment the present invention provides for a composition, an encapsulated composition and/or nanoparticles comprising, consisting essentially of, or consisting of a composition comprising an essential oil from oregano from Spain having about 63.09% of carvacrol (25 unit grams of carvacrol), an essential oil of red thyme from Spain (*Thymus vulgaris*) having about 47.37% thymol (8.75 unit grams of thymol), an essential oil from cloves of Madagascar (*Eugenia caryophyllata*) having about 85.19% eugenol (18.75 unit grams of eugenol), an essential oil of Sarriette from Albania having about 27.68% thymol (6.25 unit grams of thymol), an essential oil from ravintsara from Madagascar having about 55.26% eucalyptus (9.38 unit grams of eucalyptus), an essential oil from bay leaves from Croatia (*Laurus nobilis*) having about 48.56% cineole-1,8 (9.38 unit grams of cineole-1,8), an essential oil from Scotch pine having about 64.84% of alpha pinene (6.25 unit grams of alpha pinene), and an essential oil from green Cajeput having about 62.11% cineole, 1-8 (6.25 unit grams of cineole-1,8).

In another embodiment the present invention relates to a composition, an encapsulated composition and/or nanoparticles comprising, consisting essentially of, or consisting of about 15% by weight of an essential oil from oregano, about 70% by weight of an essential oil from clove or clove leaves and about 15% by weight of essential oil from cinnamon. The at least one antibiotic may optionally be associated with or encapsulated with the at least one essential oil.

In another aspect the present invention relates to a composition, an encapsulated composition and/or nanoparticles comprising, consisting essentially of, or consisting of about 63.28% of an essential oil extract from clove or clove leaves, 11.86% of an essential oil extract from cinnamon, 13.56% of an essential oil extract from cinnamon bark and 11.3% of an essential oil extract from rosemary or thyme.

The at least one antibiotic that can be used in the present invention can be hydrophilic or hydrophobic and includes a beta-lactamine antibiotic such as amoxicilline, amoxicilline and clavulanic acid, piperacilline which can be associated or not with tazobactam, cloxacillin, cefuroxime, cefotaxime or impenem, aminosides such as gentamicin and amikacin, a fluoroquinolone antibiotic such as ciprfloxacin, ofloxacin, a fosfomycine antibiotic, a glycopeptide antibiotic such as vancomycin and teicoplanin, a nitrofuran antibiotic, a rifamycin antibiotic, a macrolide antibiotic such as josamycin or clarithromycin, a nitro-imidazole antibiotic, a sulfamide plus a trimethoprim antibiotic, a synergistin antibiotic such as pristinamycin, their pharmaceutically acceptable salts and mixtures thereof.

The encapsulated composition of the present invention is encapsulated with a lipidic nanocapsule and has an average size of between 20 nm and 200 nm.

The nanoparticles of the present invention have an average size of between 1 nm and 100 nm or between 1 nm and 200 nm, preferably between 20 nm and 50 nm and more preferably about 50 nm.

In another embodiment the present invention provides a method for reducing and/or inhibiting and/or limiting and/or retarding the amount of infectious agent(s) and especially bacteria, parasites, fungus, undesirable vegetation, weeds and/or plant pathogens in an environment said method comprising distributing the composition, the encapsulated composition and/or nanoparticles of the present invention containing at least one essential oil or at least one essential oil extract, as described herein, and optionally at least one antibiotic as described herein, around the environment in which the infectious agent(s) need(s) to be reduced.

A method for preventing or treating a mammal, bird, reptile, fish, insect and/or plants with an infection, especially a bacterial infection, a parasitic infection, a fungal infection and/or a plant pathogen said method comprising administering to a mammal, bird, reptile, fish, insect and/or plants in need of such treatment the composition, the encapsulated composition and/or nanoparticles comprising at least one essential oil or at least one essential oil extract, as described herein, is yet another embodiment of the invention. Optionally the at least one antibiotic as described herein, that is associated with or encapsulated with the at least one essential oil or at least one essential oil extract, as described herein, may also be administered. In this embodiment the bacterial infection, parasitic infection and/or fungal infection can be a nosocomial infection or can alternatively be a plant infection.

A method for preventing or treating undesirable vegetation or weeds said method comprising placing on said undesirable vegetation or weeds the composition, the encapsulated composition and/or nanoparticles comprising at least one essential oil or at least one essential oil extract, as described herein, is yet another embodiment of the invention.

In another aspect the invention provides a method for treating a mammal, bird, reptile, fish, insect and/or plants with an infection, especially a bacterial infection, a parasitic infection, a fungal infection and/or plant infection said method comprising encapsulating at least one essential oil or at least one essential oil extract, as described herein, with a lipidic nanocapsule and/or nanoparticles, formulating said encapsulated essential oil or at least one essential oil extract and/or nanoparticles with at least one antibiotic, as described herein, to form an essential oil or at least one essential oil extract, as described herein, and antibiotic formulation and administering said formulation to a mammal, bird, reptile, fish, insect and/or plants in need of such treatment.

In another aspect the invention provides a method for treating a mammal, bird, reptile, fish, insect and/or plants with an infection, especially a bacterial infection, a parasitic infection, a fungal infection and/or plant infection said method comprising formulating at least one essential oil or at least one essential oil extract as described herein in a composition with at least one antibiotic as described herein.

A method for treating a mammal, bird, reptile, fish, insect and/or plants with an infection, especially a bacterial infection, a parasitic infection, a fungal infection and/or a plant infection said method comprising encapsulating at least one essential oil or at least one essential oil extract, as described herein, with a lipidic nanocapsule and/or nanoparticles and administering said encapsulated at least one essential oil or at least one essential oil extract, as described herein, and optionally at least one antibiotic as described herein, to a mammal, bird, reptile, fish, insect and/or plants in need of such treatment is another embodiment of the present invention. In this embodiment the at least one encapsulated essential oil or at least one essential oil extract, as described herein, and the at least one antibiotic, as described herein, can be administered together or the at least one encapsulated essential oil or at least one essential oil extract, as described herein, can be first administered and the at least one antibiotic, as described herein, can be administered after the at least one encapsulated essential oil, as described herein, or the at least one antibiotic, as described herein, is first administered and the at least one encapsulated essential oil or at least one essential oil extract, as described herein, is administered after the at least one antibiotic, as described herein, or the at least one essential oil or at least one essential oil extract, as described herein and the at least one antibiotic are encapsulated into the nanocapsule or nanoparticles together and the nanocapsule and/or nanoparticles are solely administrated.

In yet another aspect a method for treating a mammal, bird, reptile, fish, insect and/or plants with an infection, especially a bacterial infection, a parasitic infection a fungal infection and/or a plant infection said method comprising encapsulating the at least one essential oil or at least one essential oil extract, as described herein, and the at least one antibiotic, as described herein, with a lipidic nanocapsule and/or nanoparticles and administering said encapsulated composition and/or nanoparticles containing at least one essential oil or at least one essential oil extract, as described herein, and at least one encapsulated antibiotic, as described herein, to a mammal, bird, reptile, fish, insect and/or plants in need of such treatment.

In another aspect the present invention provides a method for reducing and/or inhibiting and/or limiting and/or retarding the proliferation of bacteria, parasites, fungi undesirable vegetation, weeds and/or plant pathogens said method comprising administering to a mammal, bird, reptile, fish, insect and/or plants in need of such treatment at least one essential oil or at least one essential oil extract, as described herein, which is in the form of a composition, encapsulated in a nanocapsule, encapsulated in a nanoparticle or an empty lipidic nanocapsule comprising a mixture of soybean lecithin at 69% of phosphatidylcholine, caprylic-capric acid triglycerides and a mixture of free polyethylene glycol 660 and polyethylene glycol 66-hydroxystearate.

A method for reducing and/or inhibiting and/or limiting and/or retarding the amount of bacteria, parasites, fungus, undesirable vegetation, weeds and/or plant pathogens in an environment said method comprising reducing and/or inhibiting and/or limiting and/or retarding the proliferation of bacteria, parasites, fungi and/or plant pathogens by distributing the composition, the encapsulated composition and/or nanoparticles of the present invention, as described herein, or an empty lipidic nancapsule comprising a mixture of soybean lecithin at 69% of phosphatidylcholine, caprylic-capric acid triglycerides and a mixture of free polyethylene glycol 660 and polyethylene glycol 66-hydroxystearate, in the environment.

A method for reducing and/or inhibiting and/or limiting and/or retarding the amount of bacteria, parasites, fungus, undesirable vegetation, weeds and/or plant pathogens on an object said method comprising reducing and/or inhibiting and/or limiting and/or retarding the proliferation of bacteria, parasites, fungi and/or plant pathogens by placing the composition, the encapsulated composition and/or nanoparticles of the present invention as described herein or an empty lipidic nancapsule comprising a mixture of soybean lecithin at 69% of phosphatidylcholine, caprylic-capric acid triglycerides and a mixture of free polyethylene glycol 660 and polyethylene glycol 66-hydroxystearate on or around said object.

In yet another aspect the present invention relates to a method of increasing the effectiveness of essential oils said method comprising encapsulating the at least one essential oil or at least one essential oil extract, as described herein, with a lipidic nanocapsule having an average size of between 20 nm and 200 nm.

In yet another aspect the present invention relates to a method of increasing the effectiveness of essential oils or essential oil extracts said method comprising encapsulating the at least one essential oil or at least one essential oil extract as described herein in nanoparticles of the present invention, the nanoparticles having an average size of between 1 nm and 100 nm or between 1 nm and 200 nm and preferably between about 20 nm and 60 nm and more preferably about 30 nm.

In another aspect the invention relates to a composition, an encapsulated composition and/or nanoparticles of the invention for use as a medicament, and in particular for use for preventing and/or treating an infection and especially a bacterial infection, a parasitic infection and/or a fungal infection (for example a nosocomial infection) in a mammal, bird, reptile, fish and/or insect.

In another aspect the invention relates to a composition, an encapsulated composition and/or nanoparticles of the invention for use against plant pathogens.

Use of the composition, the encapsulated composition and/or nanoparticles of the present invention for the fabrication of a medicament to prevent and/or treat infections and especially bacterial infections, a parasitic infection and/or a fungal infection in a mammal, bird, reptile, fish and/or insect is also another aspect of the present invention. In this aspect of the present invention the bacterial infection, parasitic infection and/or fungal infection can be a nosocomial infection.

Use of the encapsulated composition and/or nanoparticles of the present invention for the fabrication of a composition for use against plant pathogens is yet another aspect of the present invention.

Use of the composition, the encapsulated composition and/or the nanoparticles of the present invention and as described herein, to control bacterial resistance is another aspect of the present invention.

Use of the nanoparticles, the encapsulated composition and/or the composition, as described herein, to treat undesirable vegetation and/or weeds is yet another aspect of the present invention.

BRIEF DESCRIPTION OF THE DRAWINGS

FIG. 9 are bar graphs of various clinical studies of mice infected with *Acinetobacter baumannii* that were administered empty and encapsulated nanocapsules at various concentrations over a four day period.

FIG. 10 A are the clinical results when mice were administered 3 mg of encapsulated R07 nanocapsulels (NCL), FIG. 10B are the clinical results when mice were administered 1.5 mg of encapsulated R07 nanocapsules (NCL) and FIG. 10C are the clinical results when mice were administered 0.75 mg encapsulated R07 nanocapsules (NCL).

DESCRIPTION OF THE PREFERRED EMBODIMENTS

Figure 1:
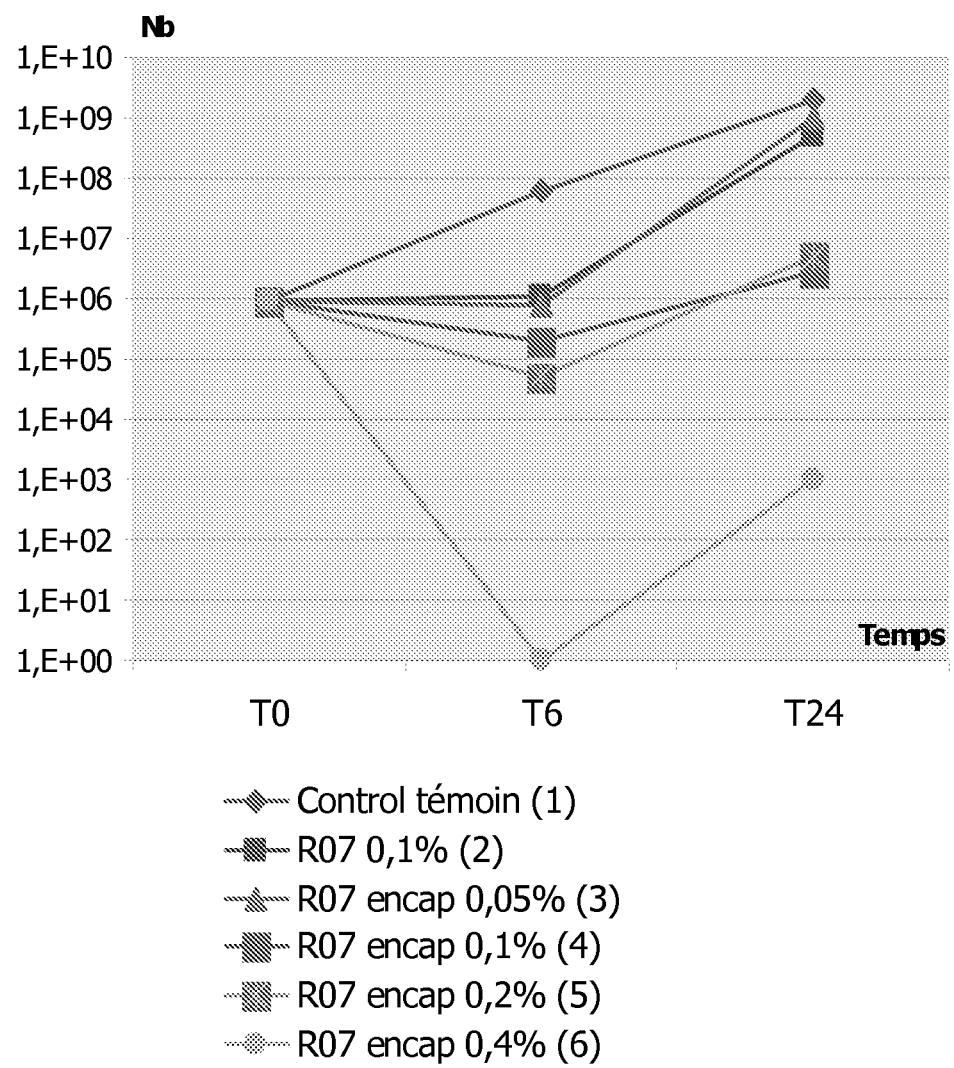
FIG. 1 is a graph showing the number of bacteria of *P. aeruginosa* at times T0, T6 (6 hours after T0) and T24 (24 hours after T0) in comparison with a control that was not exposed to either encapsulated or non encapsulated essential oil (R07). 0.1% of non encapsulated R07, 0.05% of encapsulated R07, 0.1% of encapsulated R07, 0.2% of encapsulated RO7 or 0.4% of encapsulated R07 was used.

"LNC" as used herein means lipidic nanocapsules. They are characterized as a hybrid structure between polymer nanocapsules and lipsomes and are generally prepared by solvent-free and soft energy procedures. They generally have an oily core, corresponding to medium chain triglycerides surrounded by a membrane made from a mixture of lecithin and a pegylated surfactant. The molecules enapsulated rest on the interior of the nanocapsule.

As used herein the term "nanoparticles" means having a structure possessing at least one dimension sized from 1 to 200 nanometers. In the present invention such nanoparticles are characterized by the fabrication of the nanoparticles without lipophilic Labrafac® and only with polyethylene glycol using various essential oils or extracts of essential oils. These nanoparticles are lipophilic and do not have a core of caprylic-capric acid triglycerides. Thus, the nanoparticles of the present invention are different from the lipidic nanocapsules, although fabricated using the same procedure as the nanocapsules. The core is only composed of lipophilic active compounds.

"Essential oils" as used herein are vegetal extracts, in which the carbon atoms can be in a straight chain, a branched chain or cyclic including ethers, esters, aldehydes and ketones.

As used herein "extracts of essential oils" means the concentrated form of essential oils that are separated from many essential oils and are natural in origin or the extract of essential oils can be synthesized chemically.

As used herein "O/W to W/O" when referring to emulsions means oil in water and water in oil.

The term "mammal" encompasses any of various warm-blooded vertebrate animals of the class Mammalia, including humans, characterized by a covering of hair on the skin and, in the female, milk-producing mammary glands for nourishing the young. The present invention is not limited to treating humans, but also encompasses veterinary applications, especially since it is well known that animals also can have infections and in particular bacterial infections, parasitic infections and/or fungal infections.

The term "insects" encompasses any animal of the class Insecta, comprising small, air-breathing arthropods having the body divided into three parts (head, abdomen and thorax) and having three pairs of legs and usually two pairs of wings. Examples include spiders, ticks and centipedes.

"Reptiles" encompasses any of various cold-blooded, usually egg laying vertebrates of the class Reptilia, such as snakes, lizards, crocodiles or turtles, having an external covering of scales or honey plates and breathing by means of lungs.

The term "bird" means any warm-bloodeed vertebrate of the class Ayes, having a body covered with feathers, forelimbs modified into wings, scaly legs, a beak, no teeth and bearing young in a hard-shelled egg. Some examples of birds include robins, owls, swans and cardinals.

"Fish" encompass any of various cold-blooded, aquatic vertebrates, having gills, commonly fins and typically an elongated body covered with scales that belongs to the class Agnatham Chonndrichthyes or Osteichthyes. Examples of fish include lampreys, sharks, tuna, bass, salmon and trout.

Plants encompass any of various photosynthetic, eukaryotic, multicellular organisms of the kingdom Plantae characteristically producing embryos, containing chloroplasts, having cellulose cell walls and lacking the power of locomotion.

"Broad spectrum activity" when referring to antibacterial activity, antiparasitic activity, antifungal activity, undesirable vegetation activity or weed activity and/or plant antipathogenic activity means that the essential oils or essential oil extracts have a wide range of activity against disease-causing bacterial, disease causing parasites, disease causing fungus, undesirable vegetation, weeds, and/or disease causing plant pathogens.

The term "encapsulated" means that at least one essential oil alone is in the interior of the nanocapsule or nanoparticles or in another embodiment that both the at least one antibiotic and the at least one essential oil are found on the interior of the nanocapsule or nanoparticles.

The term "R07" is an abbreviation for a composition comprising an essential oil from oregano from Morocco or the Balkans having about 33.20% or 70% of carvacrol (14.7 unit grams of carvacrol), an essential oil from clove leaves from Madagascar having 82.57% eugenol (70.6 unit grams of eugenol) and essential oil from cinnamon from China having 77.57% of trans cinnamaldehyde (14.7 unit grams of trans cinnamaldehyde). The essential oil R07 is generally administered at a dose of 37.5 mg per kg of mammal, bird, reptile, fish insect and/or plant. It is interesting to note that R07, encapsulated R07 or R07 in nanoparticles does not destroy bacterial intestinal flora when administered at a dose of 37.5 mg per kg. R07 can be encapsulated or in the form of nanoparticles.

The term "AT110" is an abbreviation for a composition comprising four essential oils extracts. AT110 comprises about 11.86% carvacrol extract (5.25 unit grams of carvacrol) from oregano, 63.28% eugenol (54.10 unit grams of eugenol) an essential oil extract from clove leaves or cloves from Madagascar, 13.56% of trans cinnamaldehyde extract (2.57 unit grams of trans cinnamaldehyde) an essential oil extract from cinnamon from China and 11.3% trans-β-caryophyllene (1.80 unit grams of trans-β-caryophyllene) from oregano, cloves and/or cinnamon. It is interesting to note that AT110 does not destroy bacterial intestinal flora when administered at a dose of about 10 to 37.5 mg per kg. AT110 can be in the form of a composition in which the above essential oil extracts are mixed in defined percentages. AT110 can also be encapsulated in a composition with or without an antibiotic, as described herein, and/or can be in the form of nanoparticles with or without an antibiotic, as described herein.

By the terminology "associated with the antibiotic" means that the antibiotic can be administered together with the at least one composition, encapsulated at least one essential oil or at least one essential oil extract and/or nanoparticles containing the at least one essential oil or essential oil extract or can be administered separately from the at least one essential oil or essential oil extract.

By "environment" is meant surroundings in which the present invention can be used.

The term "objects" as used herein includes any exterior or interior surface that may have a bacterial and/or parasitic and/or fungal infection and/or plant pathogens. Surfaces may include, for example, surgical instruments, counter tops, hospital furniture, wheel chairs, incubators, test tubes, catheters, tubes for intubation, urinary catheters, linens and the like. The term "objects" also includes the exterior and interior surfaces of mammalians, birds, reptiles, fish, insects and/or plants.

The term "at least" as used herein means one or several. In a particular embodiment of the invention, it means one, two, three, four, five, six, seven, eight, nine or ten.

"Consisting essentially of" means that other nonessential ingredients can be formulated in the composition, lipidic nanocapsules and/or nanoparticles, which ingredients do not include the main ingredients of essential oils or their extracts and/or antibiotics.

By "synergy" is meant that two or more compounds or agents interact in such a manner that their combined effect of compounds or agents, such as two or more essential oils, is greater than the algebraic sum of their individual effects. In this regard, the at least one essential oil or at least one essential oil extract and the at least one antibiotic when associated or encapsulated or in the form of nanoparticles with the at least one essential oil or at least one essential oil extract provide a synergistic effect such that reduction of the amount of antibiotic is possible.

In a particular embodiment, by "infection" it is meant an invasion and multiplication of microorganisms in a bodily part or tissue or plant, which may produce subsequent tissue injury and progress to overt disease through a variety of cellular or toxic mechanisms. In this regard, infection includes air born infections, droplet infections, endogenous infections, tunnel infections and opportunistic infections.

"Bacterial infection" as used herein means invasion of bacteria of a bodily part or tissues, which may produce tissue injury and progress to disease. Examples of bacteria that cause infections include *Streptococcus, Staphylococcus, E. coli* and the like as described herein.

By "parasitic infection" is meant an infection caused by a plant or animal that at some stage of its existence obtains nourishment from another living organism called the host. Examples are tapeworms, fleas, ticks, mosquitoes and the like that prey on hosts such as mammals.

"Fungal infection" as used herein means any inflammatory condition caused by fungus. Examples of fungal infections include thrush, ring worm, pneumonia, *Candida* yeast infection and the like.

"Plant pathogens" as used herein are any organisms that cause infectious diseases including fungi, oomycetes, bacteria, mycoplasmas, viruses, virus-like organisms, phytoplasmas, protozoa, nematodes and parasites in plants. Examples of plant pathogens, include, but are not limited to, fungi belonging to Ascomycetes and Basidiomycetes, pathogens from the genus *Phytophthora, Burkholderia, Proteobacteria, Phytoplasma* and *Spiroplasma.*

As used herein "quorum sensing" delays the virulence of pathogens by enveloping the pathogens of bacteria, parasites, fungus and/or plants when the nanocapsules or nanoparticles of the present invention described herein are used.

"Herbicide" means any chemical used to destroy or inhibit plant growth, especially of weeds or other undesirable vegetation. In this respect, the compositions, encapsulated nanocapsules and/or nanoparticles containing the at least one essential oil or the at least one essential oil extract can be used as an herbicide.

Thus, the present invention provides a composition, an encapsulated composition and/or nanoparticles comprising at least one essential oil, as described herein, or at least one essential oil extract, as described herein, having a broad spectrum antibacterial activity, antiparasitic activity, antifungal activity, undesirable vegetation or weed activity and/or plant antipathogenic activity, optionally at least one antibiotic as described herein, and optionally a pharmaceutically acceptable carrier.

The composition can comprise an essential oil from oregano from Morocco or the Balkans having about 33.20% or 70% of carvacrol (14.7 unit grams of carvacrol), an essential oil from clove leaves from Madagascar having 82.57% eugenol (70.6 unit grams of eugenol) and essential oil from cinnamon from China having 77.57% of trans cinnamaldehyde (14.7 unit grams of trans cinnamaldehyde).

The composition of the present invention can also have four essential oil extracts comprising about 11.86% carvacrol extract (5.25 unit grams of carvacrol) from oregano, 63.28% eugenol (54.10 unit grams of eugenol) an essential oil extract from clove leaves or cloves from Madagascar, 13.56% of trans cinnamaldehyde extract (2.57 unit grams of trans cinnamaldehyde) an essential oil extract from cinnamon from China and 11.3% trans-β-caryophyllene (1.80 unit grams of trans-β-caryophyllene) from oregano, cloves and/or cinnamon. This composition, as referred to herein, can be a nonencapsulated composition and can present as a liquid or formulated as suspensions, utilized alone or diluted in water or reconstituted or lyophilized.

The encapsulated composition is encapsulated with a lipidic nanocapsule, which is characterized by a hybrid structure between polymer nanocapsules and lipsomes. The lipidic nanocapsule is composed of an oily core, corresponding to medium-chain triglycerides surrounded by a membrane made of lecithin and a pegylated surfactant. Their formulation is based on a process known as the phase-inversion temperature phenomenon of emulsion leading to lipid nanocapsule formation with a good monodispersion. This process is described in WO 2009/004214 A2, which is incorporated herein by reference.

The encapsulated composition of the present invention has an average size of between 20 nm and 200 nm. However, the particle size can vary between 40 nm and 100 nm. In another aspect the size can vary between 50 nm and 180 nm.

In another aspect the at least one essential oil or at least one essential oil extract can be used to form nanoparticles having a structure possessing at least one dimension sized from 1 to 200 nanometers. In the present invention such nanoparticles are characterized by the fabrication of the nanoparticles without lipophilic Labrafac® and only with polyethylene glycol using at least one essential oil or at least one essential oil extract. These nanoparticles are lipophilic and do not have a core of caprylic-capric acid triglycerides. Thus, the nanoparticles of the present invention are different from the lipidic nanocapsules, although they are made by the same phase inversion process as that of the encapsulated nanocapsule composition.

In one aspect of the present invention only the at least one essential oil or at least one essential oil extract, as described herein, is in a composition, is encapsulated or is in the form of nanoparticles. The at least one antibiotic as described herein, then can be associated with the composition with the at least one essential oil or at least one essential oil extract in a composition as described herein, encapsulated the at least one essential oil or at least one essential oil extract, as described herein, or associated with the nanoparticles in the different embodiments of the invention.

The at least one essential oil or at least one essential oil extract that can be used in the composition, encapsulated composition and/or nanoparticles of the present invention include essential oils or essential oil extracts from oregano, essential oils from oregano or essential oil extracts from Spain or Morocco, essential oils or essential oil extracts from thyme, essential oils or essential oil extracts from cloves, essential oils or essential oil extracts from the leaves of cloves, essential oils or essential oil extracts from savory, essential oils or essential oil extracts from raventsara, essential oils or essential oil extracts from laurel leaves, essential oils or essential oil extracts from scotch pine, essential oils or essential oil extracts from eucalyptus, essential oils or essential oil extracts from paper bark, essential oils or essential oil extracts from green paper bark, essential oils or essential oil extracts from red thyme, essential oils or essential oil extracts from Sarriette, essential oils or essential oil extracts from Chinese cinnamon and essential oils or essential oil extracts from cinnamon and/or mixtures thereof.

In another aspect of the invention the at least one essential oil or at least one essential oil extract is obtained by a distillation using water vapor or any other known extraction methods and is composed of mainly phenols and aldehydyes having a relatively low molecular weight and contains terpenes (136 Da), terpenols (154 Da) and sesquiterpenes (200 Da) and is encapsulated and/or is in the form of nanoparticles. It also can be formulated without encapsulation and without nanoparticles in form of a composition.

The concentration of each of the essential oil(s) or essential oil extracts present in the composition, encapsulated composition and/or in the nanoparticles may vary independently from about 0.5% to 80% by weight, from about 1% to 40% by weight, from about 0.2% to 25% by weight, from about 0.01% to 2% by weight, from 0.05% to 0.5% by weight or from 0.05% to 1% by weight (for example an amount of 0.05% by weight, 0.1% by weight, 0.2% by weight, 0.3% by weight, 0.4% by weight or 0.5% by weight depending on the essential oil(s) used.

In one embodiment of the invention the at least one essential oil or at least one essential oil extract that can be, in the form of a composition, encapsulated and/or in the form of nanoparticles comprises, consists essentially of or consists of about 5 to about 40% by weight of essential oil or at least one essential oil extract from oregano and/or about 1% to about 25% by weight of essential oil or at least one essential oil extract from thyme and/or about 1% to 75% by weight of essential oil or at least one essential oil extract from cloves and/or about 1% to 20% by weight of essential oil or at least one essential oil extract from savory and/or about 1% to 20% by weight of essential oil or at least one essential oil extract from raventsara and/or about 1% to 20% by weight of essential oil or at least one essential oil extract from laurel leaves and/or about 1% to 20% by weight of essential oil or at least one essential oil extract from scotch pine and/or about 1% to 20% by weight of essential oil or at least one essential oil extract from paper bark and/or about 1% to 30% by weight of essential oil or at least one essential oil extract from cinnamon.

In another embodiment the at least one essential oil that can be in a composition, be encapsulated and/or in the form of nanoparticles comprises, consists essentially of or consists of about 20% to about 30% by weight of essential oil or at least one essential oil extract from oregano and/or about 3% to about 14% by weight of essential oil or at least one essential oil extract from thyme and/or about 1% to 75% by weight of essential oil or at least one essential oil extract from cloves and/or about 1% to 12% by weight of essential oil or at least one essential oil extract from savory and/or about 4% to 15% by weight of essential oil or at least one essential oil extract from raventsara and/or about 4% to 15% by weight of essential oil or at least one essential oil extract from laurel leaves and/or about 1% to 12% by weight of essential oil or at least one essential oil extract from scotch pine and/or about 1% to 12% by weight of essential oil or at least one essential oil extract from paper bark and/or about 1% to 15% by weight of essential oil or at least one essential oil extract from cinnamon.

In yet another embodiment the at least one essential oil that can be in a composition, encapsulated and/or in the form of nanoparticles comprises, consists essentially of or consists of about 25% by weight of essential oil from oregano and/or about 9% by weight of essential oil from thyme and/or about 70% by weight of essential oil from cloves and/or about 6% by weight of essential oil from savory and/or about 9% by weight of essential oil from raventsara and/or about 9% by weight of essential oil from laurel leaves and/or about 6% by weight of essential oil from scotch pine and/or about 6% by weight of essential oil from paper bark and/or about 15% by weight of essential oil from cinnamon.

In another embodiment the present invention relates to a composition, an encapsulated composition and/or nanoparticles comprising, consisting essentially of, or consisting of a composition comprising an essential oil from oregano from Morocco or the Balkans having about 33.20% or 70% of carvacrol (14.7 unit grams of carvacrol), an essential oil from clove leaves from Madagascar having about 82.57% eugenol (70.6 unit grams of eugenol) and essential oil from cinnamon from China having about 77.57% of trans cinnamaldehyde (14.7 unit grams of trans cinnamaldehyde).

About 11.86% carvacrol extract (5.25 unit grams of carvacrol) from oregano, 63.28% eugenol (54.10 unit grams of eugenol) an essential oil extract from clove leaves or cloves from Madagascar, 13.56% of trans cinnamaldehyde extract (2.57 unit grams of trans cinnamaldehyde) an essential oil extract from cinnamon from China and 11.3% trans-β-caryophyllene (1.80 unit grams of trans-β-caryophyllene) from oregano, cloves and/or cinnamon, which is encapsulated or is the form of nanoparticles or in the form of a composition is yet another aspect of the present invention.

In yet another embodiment the present invention provides for a composition, an encapsulated composition and/or nanoparticles comprising, consisting essentially of, or consisting of a composition comprising an essential oil from oregano from Spain having about 63.09% of carvacrol (25 unit grams of carvacrol), an essential oil of red thyme from Spain (*Thymus vulgaris*) having about 47.37% thymol (8.75 unit grams of thymol), an essential oil from cloves of Madagascar (*Eugenia caryophyllata*) having about 85.19% eugenol (18.75 unit grams of eugenol), an essential oil of Sarriette from Albania having about 27.68% thymol (6.25 unit grams of thymol), an essential oil from ravintsara from Madagascar having about 55.26% eucalyptus (9.38 unit grams of eucalyptus), an essential oil from bay leaves from Croatia (*Laurus nobilis*) having about 48.56% cineole-1,8 (9.38 unit grams of cineole-1,8), an essential oil from Scotch pine having about 64.84% of alpha pinene (6.25 unit grams of alpha pinene), an essential oil from green Cajeput having about 62.11% cineole, 1-8 (6.25 unit grams of cineole-1,8).

In another embodiment the present invention relates to a composition, an encapsulated composition and/or nanoparticles comprising, consisting essentially of, or consisting of a composition comprising 15% by weight of an essential oil from oregano, 70% by weight of an essential oil from clove and 15% by weight of essential oil from cinnamon. The at least one antibiotic may optionally be associated with or encapsulated with the at least one essential oil.

In another aspect the present invention relates to a composition, an encapsulated composition and/or nanoparticles comprising, consisting essentially of, or consisting of about 68.28% of an essential oil extract from clove, 11.86% % of essential oil extract from cinnamon, 13.56% of an essential oil extract from cinnamon bark and 11.3% of an essential oil extract from cloves oregano or cinnamon.

The amount of essential oil or essential oil extract which is encapsulated and/or in the form of nanoparticles may vary. Thus 50 µl to 500 µl can be encapsulated or present in the nanoparticles. In another aspect 150 µl to 250 µl can be encapsulated or present in the nanopartciles. In yet another aspect 100 µl to 200 µl of said essential oil or essential oil extract is encapsulated or present in the nanoparticles. In yet another aspect 10 µl to 2,000 µl of said essential oil or essential oil extract is encapsulated or present in the nanoparticles.

In another embodiment of the invention at least one antibiotic is encapsulated or present in the nanoparticles with at least one essential oil or at least one essential oil extract, as described above. In another embodiment the composition of at least one essential oil is mixed with the at least one antibiotic. The at least one antibiotic can be lipophilic or lypophobic. The at least one antibiotic which can be encapsulated or associated with the at least one essential oil include a beta-lactamine antibiotic such as amoxicilline, amoxicilline and clavulanic acid, piperacilline which can be associated or not with tazobactam, cloxacillin, cefuroxime, cefotaxime or impenem, aminosides such as gentamicin and amikacin, a fluoroquinolone antibiotic such as ciprfloxacin, ofloxacin, a fosfomycine antibioticm a glycopeptide antibiotic such as vancomycin and teicoplanin, a nitrofuran antibiotic, a rifamycin antibiotic, a macrolide antibiotic such as josamycin or clarithromycin, a nitroimidazole antibiotic, a sulfamide plus a trimethoprim antibiotic, a synergistin antibiotic such as pristinamycin, their pharmaceutically acceptable salts and mixtures thereof.

In one aspect the at least one antibiotic as described herein that is encapsulated or associated with the at least one essential oil or at least one essential oil extract as described herein in the composition or in the encapsulated composition or is present in the nanoparticles or associated with the nanoparticles and the at least one essential oil or at least one essential oil extract as described herein is selected from meropenem and its pharmaceutically acceptable salts. In another embodiment the at least one antibiotic that is encapsulated or associated with the at least one essential oil or at least one essential oil extract as described herein in the composition or in the encapsulated composition or is present in the nanoparticles or associated with the nanoparticles and the at least one essential oil or at least one essential oil extract as described herein is selected from rifampicin and its pharmaceutically acceptable salts. In yet another embodiment the at least one antibiotic that is encapsulated or associated with the at least one essential oil or at least one essential oil extract as described herein in the composition or in the encapsulated composition or is present in the nanoparticles or associated with the nanoparticles and the at least one essential oil or at least one essential oil extract as described herein is selected from tigecycline and its pharmaceutically acceptable salts. Mixtures of meropenem, rifampicin and tigecycline and their pharmaceutically acceptable salts thereof form another aspect of the present invention.

The composition having at least one essential oil or at least one essential oil extract as described herein alone or at least one essential oil or at least one essential oil extract as described herein and the at least one antibiotic as described herein formulated together or the encapsulated composition either having the at least one essential oil or at least one essential oil extract as described herein encapsulated alone or the at least one essential oil or at least one essential oil extract as described herein and the at least one antibiotic as described herein encapsulated together can be further formulated and be administered as a medicament. Likewise the nanoparticles having the at least one essential oil or at least one essential oil or at least one essential oil extract as described herein alone or the at least one essential oil or at least one essential oil extract as described herein and at least one antibiotic as described herein together can be further formulated and administered as a medicament. In this aspect of the present invention the encapsulated composition and/or the nanoparticles can be formulated to be delivered orally, mucosally, in a patch, in an aerosol, intravenously, topically, in a diffuser and the like. Methods for these formulations are well known in the art.

A pharmaceutically acceptable carrier can also be added to the formulation.

For example, the pharmaceutically acceptable carrier can be saline or buffered saline.

In another aspect the composition of at least one essential oil or at least one essential oil extract as described herein alone or formulated with the at least one essential oil or at least one essential oil extract as described herein and at least one antibiotic as described herein or the encapsulated formulation either having the at least one essential oil or at least one essential oil extract as described herein encapsulated alone or the at least one essential oil or at least one essential oil extract as described herein and the at least one antibiotic as described herein encapsulated together or the nanoparticles having the at least one essential oil alone or at least one essential oil extract alone as described herein or the at least one essential oil or at least one essential oil extract as described herein and at least one antibiotic as described herein together can be formulated in a spray, aerosol or slow release matrix or patch. It will be appreciated that such a formulation is for distribution around a particular environment such as hospital surfaces or sprayed into the air or used in a diffuser when this application is appropriate.

To treat plant pathogens, the composition either having the at least one essential oil or at least one essential oil extract or the at least one essential oil or at least one essential oil extract as described herein and the at least one antibiotic as described herein, the encapsulated composition either having the at least one essential oil or at least one essential oil extract as described herein encapsulated alone or the at least one essential oil or at least one essential oil extract as described herein and the at least one antibiotic as described herein encapsulated together and/or the nanoparticles having the at least one essential oil or at least one essential oil extract as described herein alone or the at least one essential oil or at least one essential oil extract as described herein and at least one antibiotic as described herein together can be formulated in a spray, aerosol or liquid form.

All of the compositions described herein, including the encapsulated compositions and the nanoparticles when used with the antibiotics described herein do not destroy bacterial intestinal flora when administered to mammals, birds, reptiles, fish and/or insects. It is well known that altering the number of gut bacteria by taking broad-spectrum antibiotics may affect the health of host and the ability to digest food. The intestinal flora helps maintain high energy levels, enhances immune function and destroys cancer causing compounds in the colon. Changing the number of gut flora by ingesting antibiotics can reduce the hosts ability to ferment carbohydrates, metabolize bile acids and may cause diarrhea. Hence, the compositions of the present invention, as described herein, when administered with antibiotics as described herein, provide the host an unexpected benefit.

Thus, in another aspect the present invention provides a method for maintaining intestinal flora in mammals, fish, birds, reptiles and/or insects, said method comprising administering to a mammal, fish, birds, reptiles and/or insect the composition of at least one essential oil or at least one essential oil extract as described herein and antibiotic as described herein or the encapsulated formulation either having the at least one essential oil or at least one essential oil extract as described herein encapsulated alone and associated with the at least one antibiotic as described herein or the at least one essential oil or at least one essential oil extract as described herein and the at least one antibiotic as described herein encapsulated together or the nanoparticles having the at least one essential oil or at least one essential oil extract as described herein and the at least one antibiotic associated with the nanoparticles or the at least one essential oil or at least one essential oil extract as described herein and at least one antibiotic as described herein encapsulated together.

In another aspect the present invention provides a method for reducing the amount of infectious agent(s) and especially the amount of bacteria, fungus, parasites, undesirable vegetation, weeds and/or plant pathogens in an environment said method comprising distributing the composition, the encapsulated composition or nanoparticles of the present invention around the environment in which the infectious agent(s) need(s) to be reduced. In this embodiment the composition, the encapsulated composition or nanoparticles contain(s) only at least one essential oil or at least one essential oil extract as described herein.

Thus, the encapsulated composition can be distributed on surfaces, in the air, in water, on objects, on plants and the like.

In a particular embodiment of the invention, the bacteria to be reduced is a gram positive bacteria selected, for example, from the family of Staphylococcaceae, bacteria from the family of Enterococcaceae, bacteria from the family of Clostridiaceae, bacteria from the family of Streptococcaceae, bacteria from the family of Aerococcaceae, bacteria from the family of Micrococcaceae, bacteria from the family of Lactobacillaceae, bacteria from the family of Nocardiaceae, bacteria from the family of Listeriaceae, bacteria from the family of Corynebacteriaceae, bacteria from the family of Bacillaceae and bacteria from the family of Propionibacteriaceae.

In another aspect the bacteria to be reduced is from the genus *Peptococcus*.

In another aspect the bacteria to be reduced is a gram positive bacteria selected from the group of: *Staphylococcus aureus, Staphylococcus epidermidis, Enterococcus faecalis, Enterococcus faecium, Enterococcus avium, Enterococcus gallinarum, Clostridium difficile, Streptococcus pneumoniae, Streptococcus agalactiae, Streptococcus viridans, Streptococcus pyogenes, Aerococcus viridans, Norcadia asteroides, Nocardia brasiliensis, Nocardia caviae, Listeria monocytogenes, Bacillus anthracis, Bacillis cereus* and *Propionibacterium*.

In yet another aspect of the invention the bacteria is a gram negative bacteria and for example is selected from the group of bacteria from the family of Moraxellaceae, bacteria from the family of Legionellaceae, bacteria from the family of Enterobacteriaceae, bacteria from the family of Pseudomonadaceae, bacteria from the family of Alcaligenaceae, bacteria from the family of Sphingomonadaceae, bacteria from the family of Pasteurellaceae, bacteria from the family of Neisseriaceae, bacteria from the family of Pasteurellaceae, bacteria from the family of Flavobacteriaceae, bacteria from the family of Bacteroidaceae and bacteria from the family of Fusobacteriaceae.

In still yet another aspect of the present invention the bacteria is a gram negative bacteria selected from the group of: bacteria from the genus *Klebsiella*, bacteria from the genus *Serratia*, bacteria from the genus *Citrobacter*, bacteria from the genus *Salmonella*, bacteria from the genus *Shigella*, bacteria from the genus *Proteus*, bacteria from the genus *Haemophilus*, bacteria from the genus *Campylobacter*, bacteria from the genus *Legionella*, bacteria from the genus *Sphingomonas* bacteria from the genus *Moraxella*, bacteria from the genus *Kingella*, bacteria from the genus *Pasteurella*, bacteria from the genus *Capnocytophaga*, bacteria from the genus *Neisseria*, bacteria from the genus *Bacteroides*, bacteria from the genus *Enterobacter*, bacteria from the genus *Pseudomonas*, bacteria from the genus *Fusobacterium*, bacteria from the genus *Achromobacter*, bacteria from the genus *Escherichia* and bacteria from the genus *Acinetobacter*.

In another aspect of the invention the bacteria is a gram negative bacteria selected from the species of: *Klebsiella pneumoniae, Klebsiella oxytoca, Acinetobacter baumannii, Acinetobacter calcoaceticus, Serratia marcescens, Citrobacter freundii, Citrobacter koseri, Haemophilus influenzae, Haemophilus parainfluenza, Campylobacter jejuni, Campylobacter coli, Legionella pneumophila, Legionella longbeachae, Legionella bozmanii, Legionella micdadei, Enterobacter cloacae, Escherichia coli, Escherichia hermannii, Pseudomonas aeruginosa, Pseudomonas fluorescens, Pseudomonas putida, Pseudomonas stutzeri, Achromobacter xylosoxidans, Achromobacter denitrificans, Sphingomonas paucimobilis, Moraxella catarrhalis, Kingella kingae, Pasteurella multicida, Capnocytophaga canimorsus, Neisseria gonorrhoeae, Neisseria lactamica* and *Bacteroides fragilis*.

In a particular embodiment of the invention, the bacteria is a *Pseudomonas aeruginosa* or an *Acinetobacter baumannii* bacteria (e.g., *Acinetobacter baumannii* 5377 or *Acinetobacter baumannii* mucoid).

The parasitic infections which can be reduced by the composition, the encapsulated composition and/or nanoparticles disclosed herein include pinworm, *Enterobius ver-micularis, Trichomonas vaginalis*, toxoplasmosis, and enteric parasites such as *Giardia lamblia* and *Cryptosporidium* spp. Taxonomically, parasites can be divided into two major groups which are Protozoa and Helminths (worms).

The characteristics of protozoan and helminthic infections vary in important ways. Protozoa are single-celled organisms that multiply by simple binary division and can multiply in their human hosts, increasing in number to cause overwhelming infection. With rare exceptions, protozoan infections do not cause eosinophilia.

Helminths (worms) are multicellular and have complex organ systems. Helminths can be further divided into roundworms and flatworms (platyhelminthes), which include tapeworms and flukes.

In contrast to protozoa, helminths do not multiply in humans but can elicit eosinophilic responses when they migrate through tissue. Most helminths have complex life cycles that involve substantial time outside their human hosts.

The fungus that can be reduced can be either a superficial fungus present on skin nails or mucous membrane or yeast infections or it can be deep and systemic fungal infections such as lung infections that produce coughing, fever, muscle aches, headaches and rashes, blood infections such as septicaemia and central nervous system infections such as meningitis.

The plant pathogens that can be reduced include fungi from the class Ascomycetes such as *Fusarium* spp, *Thielaviopsis* spp, *Verticillium* spp and *Magmaporth grisea*. Other fungus from the Basiodiomycetes class that can be reduced include *Rhizoctonia* spp, *Puccinia* spp and *Phakospora pachyrhizi*.

Other plant pathogens that can be reduced by the various compositions described herein include oomycetes, which are fungus-like organisms. Examples of oomycetes plant pathogens include *Phythium* spp and *Phtyphthora* spp.

Most plant bacteria pathogens are rod shaped bacilli and have specific pathognecity factors such as cell wall degrading enzymes, toxins, effector proteins, phytohormones and exopolysaccharides. Examples include *Phytoplasmas* and *Spiroplasma*.

Additional plant pathogens include plant viruses, viroids, virus-like organisms, neamtodes, protozoa and parasitic plants such as mistletoe and dodder.

In yet another aspect the present invention provides a method for preventing or treating a mammal, an insect, a reptile, a bird, fish, undesirable vegetation, weeds and/or a plant with an infection, especially a bacterial infection, a parasitic infection, a fungal infection and/or a plant pathogen said method comprising administering to a mammal an insect, a reptile, a bird, fish and/or a plant in need of such treatment the composition, the encapsulated composition and/or the nanoparticles of the present invention as described herein. In this embodiment the at least one essential oil or at least one essential oil extract, as described herein, can be encapsulated or non encapsulated or can be present in the form of nanoparticles and the at least one antibiotic as described herein associated with the composition, the encapsulated composition and/or nanoparticles or the at least one essential oil or at least one essential oil extract as described herein and the at least one antibiotic as described herein can both be present in the composition, the encapsulated composition or in the form of nanoparticles. Also this method can treat the various bacteria, parasites, fungus, undesirable vegetation, weeds and/or plant pathogens described above.

A method for treating a mammal, bird, reptile, fish, insect and/or plant with an infection (especially a bacterial infection parasitic infection, fungal infection, undesirable vegetation, weeds and/or plant pathogen) said method comprising encapsulating at least one essential oil or at least one essential oil extract, as described herein, with a lipidic nanocapsule and administering said encapsulated at least one essential oil or at least one essential oil extract, as described herein, associated with at least one antibiotic, as described herein, which is not encapsulated, to a mammal, bird, reptile, fish, insect and/or plant in need of such treatment is another aspect of the present invention. In this particular aspect the encapsulated at least one essential oil or at least one essential oil extract, as described herein, and at least one antibiotic as described herein are administered together or the at least one essential oil or at least one essential oil extract, as described herein, is first administered and the at least one antibiotic, as described herein, is administered after the at least one essential oil or at least one essential oil extract or the at least one antibiotic, as described herein, is first administered and the at least one essential oil or at least one essential oil extract, as described herein, is administered after the at least one antibiotic as described herein. In this aspect the at least one essential oil or at least one essential oil extract, as described herein, and the at least one antibiotic as described herein can be used in this embodiment. Also this method can treat the various bacteria, parasite, fungus, undesirable vegetation, weeds and/or plant as described above.

A method for treating a mammal, bird, reptile, fish, insect and/or plant with an infection or undesirable vegetation and/or weeds (especially a bacterial infection, parasitic infection, fungal infection and/or plant pathogen) said method comprising providing at least one essential oil or at least one essential oil extract, as described herein, in the form of nanoparticles and administering said encapsulated at least one essential oil or at least one essential oil extract, as described herein, associated with at least one antibiotic, as described herein, which is not encapsulated, to a mammal, bird, reptile, fish, insect undesirable vegetation, weeds and/ or plant in need of such treatment is another aspect of the present invention. In this particular aspect the nanoparticles having at least one essential oil or at least one essential oil extract, as described herein, and at least one antibiotic as described herein are administered together or the at least one essential oil or at least one essential oil extract, as described herein, is first administered and the at least one antibiotic, as described herein, is administered after the at least one essential oil or at least one essential oil extract, as described herein, or the at least one antibiotic as described herein is first administered and the at least one essential oil or at least one essential oil extract, as described herein, is administered after the at least one antibiotic as described herein. In this aspect the at least one essential oil or at least one essential oil extract, as described herein, and the at least one antibiotic described above can be used in this embodiment. Also this method can treat the various bacteria, parasite, fungus undesirable vegetation, weeds and/or plant pathogens as described above.

In yet another aspect the present invention provides a method for reducing and/or inhibiting and/or limiting and/or retarding the proliferation of bacteria, parasites, fungus, undesirable vegetation, weeds and/or plant pathogens said method comprising administering to a mammal, insects, birds, fish and/or plants in need of such treatment a composition having at least one essential oil or at least one essential oil extract, as described herein, encapsulated essential oil or at least one essential oil extract, as described herein, and/or nanoparticles as described herein or an empty lipidic nanocapsule comprising a mixture of soybean lecithin at 69% of phosphatidylcholine, caprylic-capric acid triglycerides and a mixture of free polyethylene glycol 660 and polyethylene glycol 66-hydroxystearate as described herein.

A method for reducing and/or inhibiting and/or limiting and/or retarding the amount of bacteria, parasites, fungus, undesirable vegetation, weeds and/or plant pathogens in an environment said method comprising reducing and/or inhibiting and/or limiting and/or retarding in bacteria, parasites, fungus, undesirable vegetation, weeds and/or plant pathogens by distributing the compositions, the encapsulated compositions and/or the nanoparticles of the present invention as described herein or an empty lipidic nanocapsule comprising a mixture of soybean lecithin at 69% of phosphatidylcholine, caprylic-capric acid triglycerides and a mixture of free polyethylene glycol 660 and polyethylene glycol 66-hydroxystearate in the environment.

A method for reducing and/or inhibiting and/or limiting and/or retarding the amount of bacteria, parasites, fungus, undesirable vegetation, weeds and/or plant pathogens on an object said method comprising reducing and/or inhibiting and/or limiting and/or retarding in bacteria, parasites, fungus, undesirable vegetation, weeds and/or plant pathogens by placing the composition, the encapsulated composition and/or the nanoparticles of the present invention, as described herein, or an empty lipidic nanocapsule comprising a mixture of soybean lecithin at 69% of phosphatidylcholine, caprylic-capric acid triglycerides and a mixture of free polyethylene glycol 660 and polyethylene glycol 66-hydroxystearate on or around said object.

The encapsulated composition is administered at a dose depending upon the at least one essential oil(s) or at least one essential oil extract. as described, herein that is administered, encapsulated and/or in the form of nanoparticles and/or the at least one antibiotic(s) as described herein that are associated with the composition, encapsulated composition and/or nanoparticles having at least one essential oil or at least one essential oil extract, as described herein, or at least one essential oil or at least one essential oil extract, as described herein, and the at least one antibiotic as described herein are encapsulated or in the form of nanoparticles and the infection and/or plant pathogens (especially the bacterial, parasitic, fungal infections, undesirable vegetation, weeds and/or plant pathogens) to be treated. Thus, it is well known in the art that to treat pneumonia a different dosage of antibiotic is used than to treat a urinary infection. For instance the aminoglycoside gentamicin is generally administered at a dose of 5 mg/kg in a single daily dose. However due to the synergistic effects of the combination with the at least one essential oil and encapsidation of the composition a dose between 1 mg/kg to 3 mg/kg can be used.

In all the methods described herein the bacterial infections, parasitic infections and/or fungal infections can derive from a nosocomial infection. Cumulatively or alternatively, in these methods the mammal can be a human or a mammal. Cumulatively or alternatively, in these methods the encapsulated composition can administered orally or mucosally or through an aerosol, or intravenously or topically.

In another embodiment the present invention provides a method of increasing the effectiveness of the at least one essential oil or at least one essential oil extract, as described herein, (or a method of reducing the amount of this at least one essential oil(s) or at least one essential oil extract) in a composition said method comprising encapsulating the essential oils or at least one essential oil extract, as described herein, with a lipidic nanocapsule having a size of between 20 nm and 200 nm or formulating the at least one essential oil or at least one essential oil extract in nanoparticles.

A method of reducing the amount of an antibiotic in a medicament said method comprising adding a composition having at least one essential oil or at least one essential oil extract, as defined herein, an encapsulated composition having at least one essential oil or at least one essential oil extract, as described herein, and/or nanoparticles having at least one essential oil or at least one essential oil extract, as defined herein, with the at least one antibiotic as described herein, which is either encapsulated or associated with the at least one essential oil or at least one essential oil extract present in the composition, the encapsulated composition and/or the nanoparticles.

In another aspect the present invention relates to a composition, an encapsulated composition and/or nanoparticles as disclosed herein for use as a medicament and especially for use for preventing and/or treating infections and especially bacterial infections, parastic infections and/or fungal infections in a mammal, bird, reptile, fish and/or insect.

The present invention also relates to a composition, an encapsulated composition and/or nanoparticles as disclosed herein for use as a composition to treat plant pathogens and especially for use for preventing and/or treating in plants fungi, oomycetes, bacteria, viruses, nematodes, protozoa and parasitic plants.

The present invention relates to a method to treat undesirable vegetation and/or weeds by placing the composition, an encapsulated composition and/or nanoparticles as disclosed herein on said undesirable vegetation and/or weeds.

Use of the composition, encapsulated composition and/or nanoparticles as described herein for the fabrication of a medicament or a composition to prevent and/or treat plant diseases or intended to prevent and/or treat infections and especially bacterial infections, parastic infections and/or fungal infections in a mammal, bird, reptile, fish and/or insect is also an aspect of the present invention. In this regard the at least one essential oil and the at least one antibiotic described above can be used in these embodiments. Also these embodiments can be performed to treat the various bacteria, parasitic, fungal infections and/or plant pathogens described above. Also the bacterial, parasitic and/or fungal infections can be a nosocomial infection.

Use of the composition, encapsulated composition and/or nanoparticles as described herein to maintain intestinal floral in a mammal, bird, reptile, fish and/or insect is another aspect of the invention.

Use of the composition, encapsulated composition and/or nanoparticles, as described herein, to control bacterial resistance is yet another aspect of the present invention.

Use of the nanoparticles, the encapsulated composition and/or the composition, as described herein, to treat undesirable vegetation and/or weeds is another aspect of the invention.

A number of embodiments and/or aspects of the invention have been described. Nevertheless it will be understood that various modifications may be made without departing from the spirit and scope of the invention.

EXAMPLES

Example 1

Preparation of Basic Microemulasion Obtained by a Phase Inversion Method (Empty Lipid Nanocapsules)

5 g of an emulsion containing 75 mg of Lipoïd S75-3® (soybean lecithin at 69% of phosphatidylcholine), 504 mg of lipophilic Labrafac WL 1349® (caprylic-capric acid triglycerides), 504 mg of Solutol HS® (a mixture of free polyethylene glycol 660 and polyethylene glycol 66-hydroxystearate), 15.383 g of water and 88 mg of sodium chloride were prepared.

All of the above ingredients were placed in the same beaker under magnetic stirring.

Heat was then applied until a temperature of 85° C. was reached. With continued magnetic stirring, the system was allowed to cool to a temperature of 60° C. These heating cycles (between 85° C. and 60° C.) were performed three times so as to obtain microemulsions that are more and more structured.

The system was then maintained in its microemulsion form by stabilizing it at a temperature that is within or close to the phase inversion zone, in the present case 65° C.

The empty nanocapsules are formulated after cooling a dilution of the basic microemulsion.

The different suspensions were utilized alone or diluted in water or reconcentrated or lyophilized.

Example 2

Preparation of Empty Lipophilic Nanocapsules Charged With Essential Oil (R07)

Nanocapsules with an average size of 50 nm and charged with 100 µl or 200 µl of essential oil (R07) were prepared. The composition R07 comprised an essential oil from oregano from Morocco or the Balkans having about 33.20% or 70% of carvacrol (14.7 unit grams of carvacrol), an essential oil from clove leaves from Madagascar having 82.57% eugenol (70.6 unit grams of eugenol) and essential oil from cinnamon from China having 77.57% of trans cinnamaldehyde (14.7 unit grams of trans cinnamaldehyde).

100 µl or 200 µl of R07 were added to the microemulsion obtained by phase inversion as that described in example 1 at 45° C. at a concentration of 115 g/l. The R07 was encapsulated into the nanocapsules after dilution or cooling of the loaded R07 microemulsion.

Example 3

Preparation of the Composition AT110

About 11.86% carvacrol extract (5.25 unit grams of carvacrol) from oregano, 63.28% eugenol (54.10 unit grams of eugenol) an essential oil extract from clove leaves or cloves from Madagascar, 13.56% of trans cinnamaldehyde extract (2.57 unit grams of trans cinnamaldehyde) an essential oil extract from cinnamon from China and 11.3% trans-β-caryophyllene (1.80 unit grams of trans-β-caryophyllene) from oregano, cloves and/or cinnamon are mixed together to form the composition AT110.

Example 4

Preparation of Nanoparticles

Between 5% and 20% of Solutol HS® (a mixture of free polyethylene glycol 660 and polyethylene glycol 66-hydroxystearate) between 1% and 5% of Lipoïd S75-3® (soybean lecithin at 69% of phosphatidylcholine), between 1 and 10% of sodium chloride, between 10 and 20% of AT110 or R07 and water were prepared.

All of the above ingredients were placed in the same beaker under magnetic stirring.

Heat was then applied until a temperature of 85° C. was reached. With continued magnetic stirring, the system was allowed to cool to a temperature of 60° C. These heating cycles were performed three times so as to obtain microemulsions that are more and more structured.

The system was then maintained in its microemulsion form by stabilizing it at a temperature that is within or close to the phase inversion zone.

This system is then cooled and/or diluted in order to obtain a suspension or loaded nanoparticle.

Example 5

Kinetic Studies of the Encapsulated Essential Oil (R07) and Non-Encapsulated Oil (RO7) on Pseudomonas aeruginosa The bacterial strain of Pseudomonas aeruginosa that was used was a suspension of 0.5 MF (Mac Farland) corresponding to $2 \times 10^8$ CFU (colony forming unit). The final inoculum corresponded to a dilution of $1/100^e$ of MF and thus about $2 \times 10^6$ CFU/ml.

The non encapsulated essential oil was first diluted prior to its use by taking 2 ml of essential oil (R07) to which 3 ml of DMSO was added. 1 ml of the diluted essential oil was then diluted with 3 ml of Muller-Hilton broth for a solution of 100 mg/l or 100 µg/ml, which corresponded to a concentration of 10%. The final concentrations of 0.05% to 0.5% were obtained by first diluting the 10% solution is sterile mineral water and the final dilutions in Muller-Hilton broth.

The encapsulated and nonencapsulated essential oils were tested at subinhibtory concentrations (a concentration that is immediately inferior to the effective concentration) so that an eventual synergy or indifference or antagonistic association can be recognized.

The bacterial strain was placed in a Muller-Hilton broth and contacted with either the encapsulated R07 essential oil or the non encapsulated essential oil, diluted as set forth above. The number of bacteria was measured at time zero (T0), 6 hours after T0(T6) and 24 hours after T0 (T24).

Figure 2:
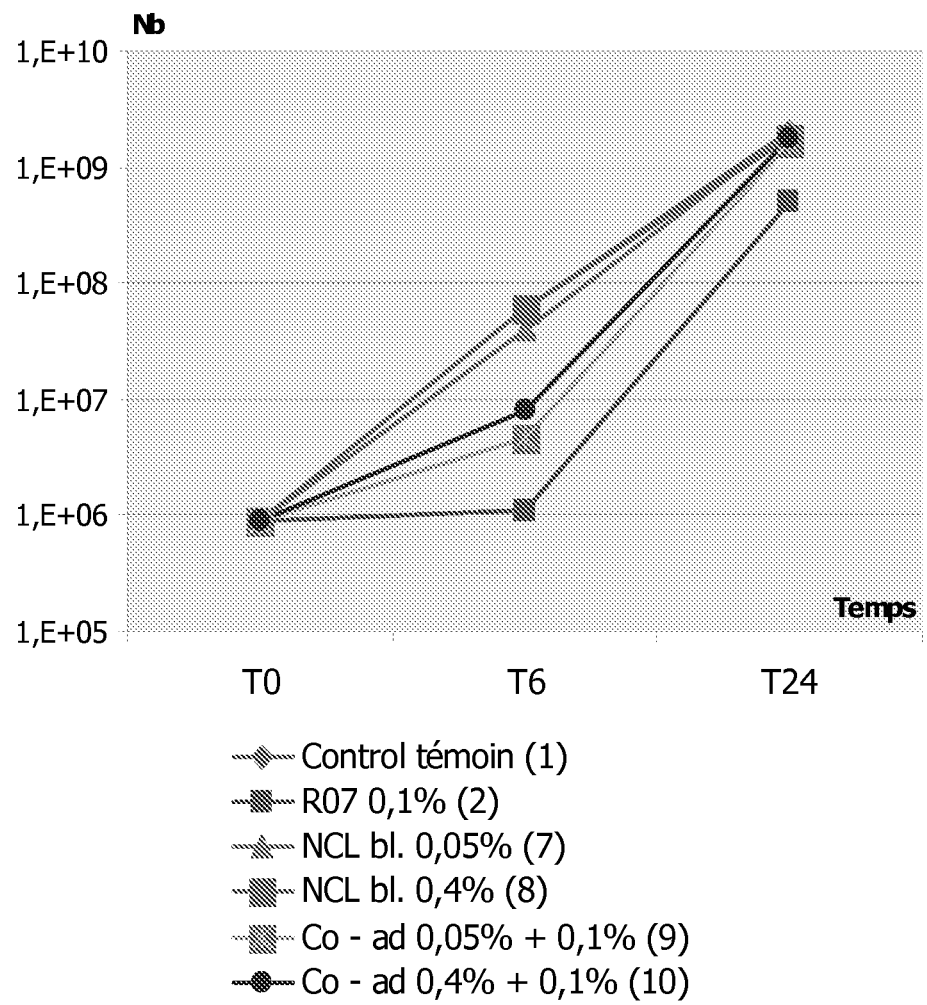
FIG. 2 is a graph showing the number of bacteria *P. aeruginosa* at times T0, T6 (6 hours after T0) and T24 (24 hours after T0) in comparison with a control that was not exposed to either encapsulated or non encapsulated essential oil (R07). 0.1% of non encapsulated R07, 0.05% of an empty lipid nanocapsule with no essential oil or 0.4% of an empty lipid nanocapsule with no essential oil was used. Co-administration of 0.05% or 0.4% of said empty lipid nanocapsule and 0.1% of non encapsulated R07 was also performed.
Figure 3:
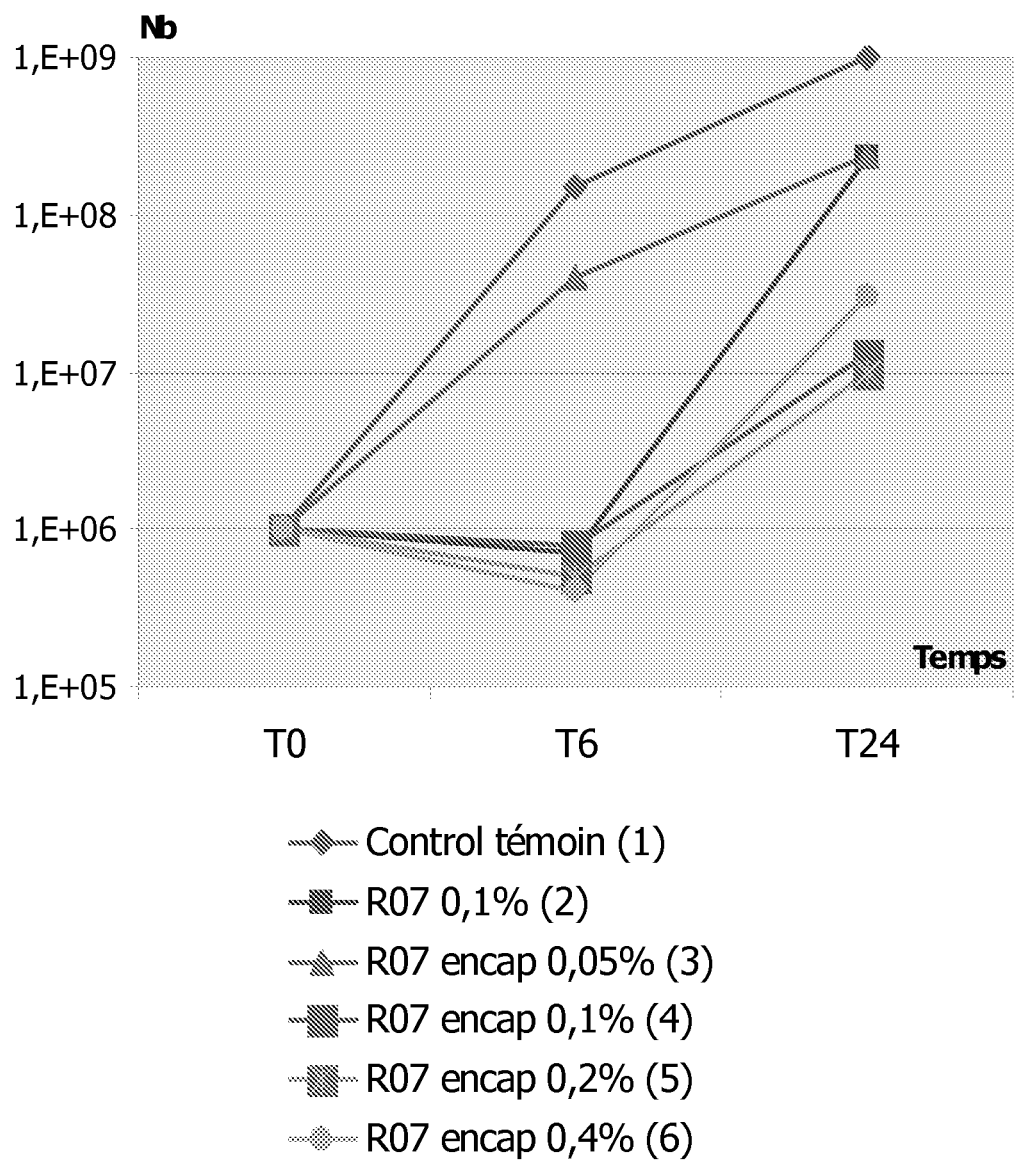
FIG. 3 is a graph showing the number of bacteria of *A. baumannii* 5377 at times T0, T6 (6 hours after T0) and T24 (24 hours after T0) in comparison with a control that was not exposed to either encapsulated or non encapsulated essential oil (R07). 0.1% of non encapsulated R07, 0.05% of encapsulated R07, 0.1% of encapsulated R07, 0.2% of encapsulated RO7 or 0.4% of encapsulated R07 was used.
Figure 4:
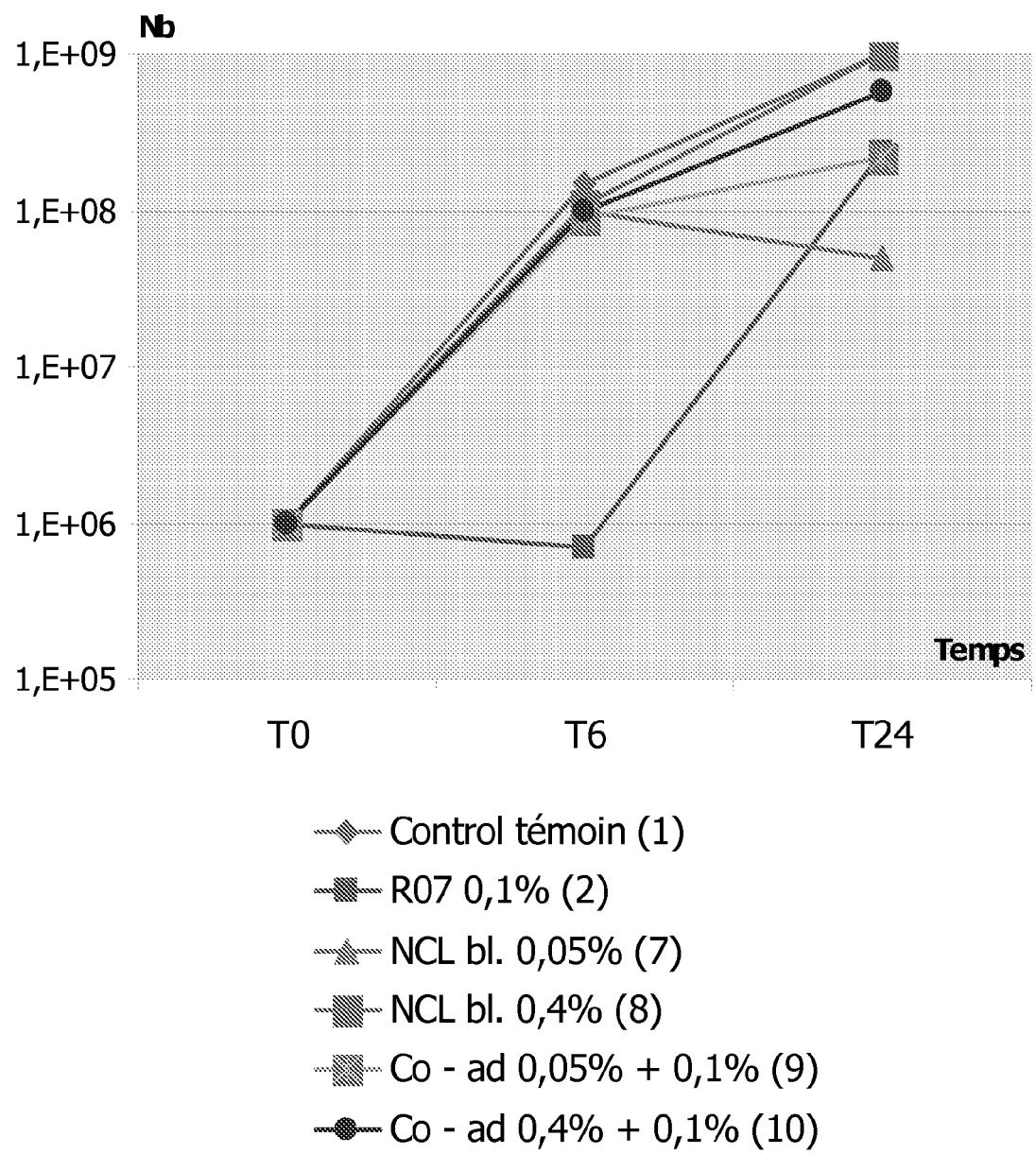
FIG. 4 is a graph showing the number of bacteria *A. baumannii* 5377 at times T0, T6 (6 hours after T0) and T24 (24 hours after T0) in comparison with a control that was not exposed to either encapsulated or non encapsulated essential oil (R07). 0.1% of non encapsulated R07, 0.05% of a empty lipid nanocapsule with no essential oil or 0.4% of a empty lipid nanocapsule with no essential oil was used. Co-administration of 0.05% or 0.4% of said empty lipid nanocapsule and 0.1% of non encapsulated R07 was also performed.
Figure 5:
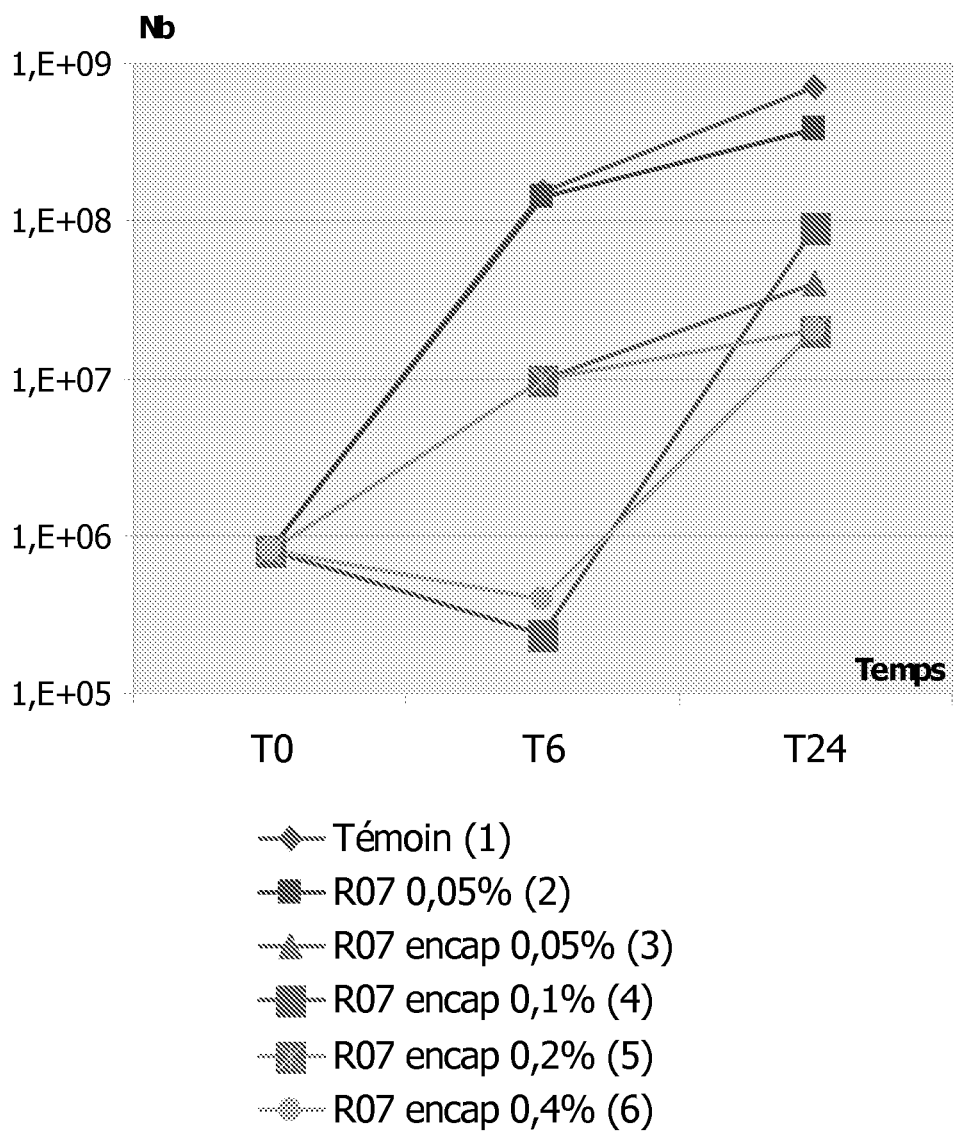
FIG. 5 is a graph showing the number of bacteria of *A. baumannii* mucoid at times T0, T6 (6 hours after T0) and T24 (24 hours after T0) in comparison with a control that was not exposed to either encapsulated or non encapsulated essential oil (R07). 0.05% of non encapsulated R07, 0.0.5% of encapsulated R07, 0.1% of encapsulated R07, 0.2% of encapsulated RO7 and 0.4% of encapsulated R07 was used.
Figure 6:
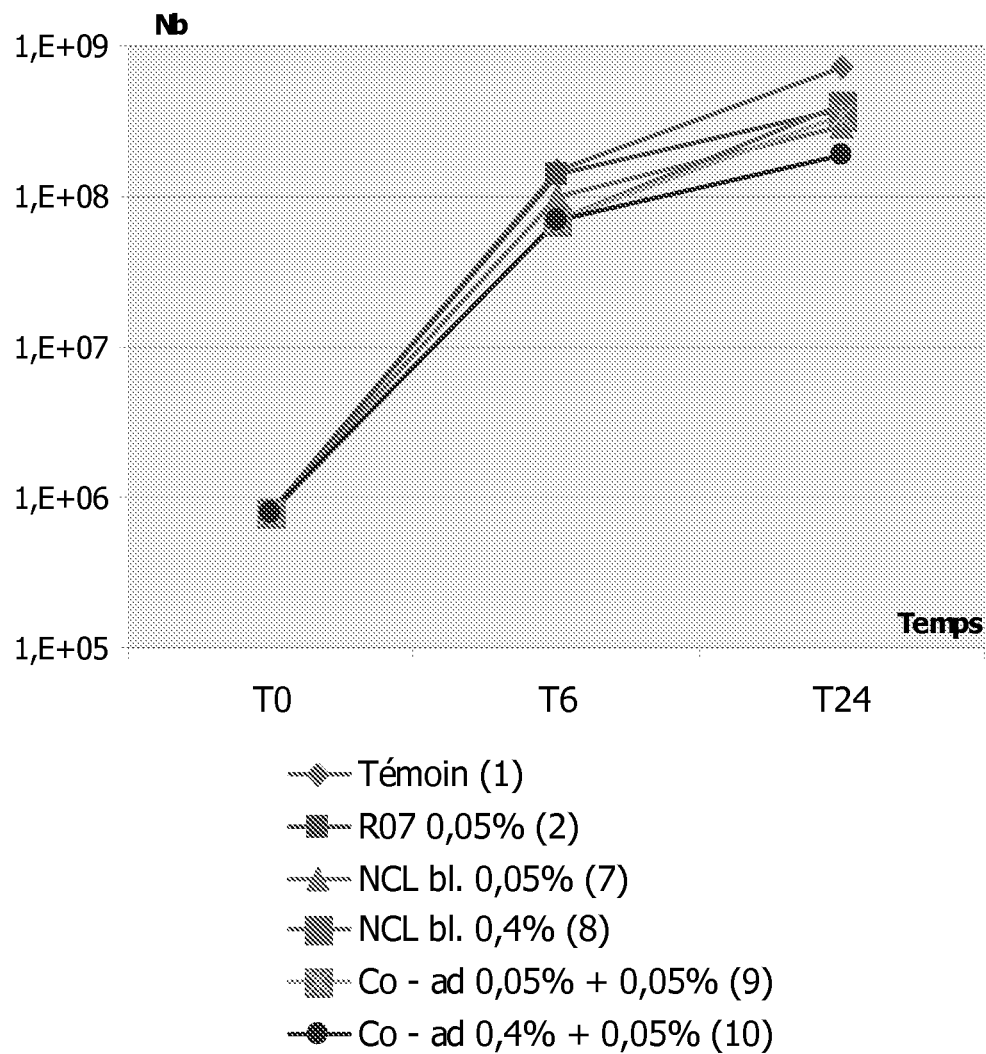
FIG. 6 is a graph showing the number of bacteria *A. baumannii* mucoid at times T0, T6 (6 hours after T0) and T24 (24 hours after T0) in comparison with a control that was not exposed to either encapsulated or non encapsulated essential oil (R07). 0.1% of the essential oil R07, 0.05% of a empty nanocapsule lipid with no essential oil or 0.4% of a empty nanocapsule lipid with no essential oil was used. Co-administration of 0.05% or 0.4% of said empty lipid nanocapsule and 0.1% of non encapsulated R07 was also performed.

The results are shown in FIGS. 1 and 2. In FIG. 1 there exists a difference of 0.7 log between the activity of the essential oil R07 non-encapsulated and the essential oil R07 encapsulated at a concentration of 0.1% for the encapsulated formulation at T6. This difference is even more noticeable at 24 hours where there is more rapid regrowth with the non-encapsulated essential oil R07 leading to a difference of 2 logs, which a factor of 100. At a 0.1% concentration in the encapsulated essential oil it was demonstrated that there was bacterostatic activity in a bacterial strain that is known to be multi-resistant towards antibiotics. An excellent bactericidal activity exists in the encapsulated formulation at 0.4% essential oil R07.

The different suspensions were utilized alone or diluted in water or reconcentrated or lyophilized.

Example 6

Kinetic Studies of the Encapsulated Essential Oil (RO7) and non-encapsulated oil (RO7) on Acinetobacter baumannii 5377

This bacteria, Acinetobacter baumannii 5377, was chosen since it is known as a bacteria that is responsible for nocosomial and for epidemic outbreaks in hospitals, This bacteria can adapt to its environment and is a bacteria that is multiresistant to antibiotics.

The bacterial strain of Acinetobacter baumanni 5377 that was used was a suspension of 0.5 MF (Mac Farland) corresponding to $2 \times 10^8$ CFU (colony forming unit). The final inoculum corresponded to a dilution of $1/100^e$ of MF and thus about $2 \times 10^6$ CFU/ml.

The non encapsulated essential oil (R07) was first diluted prior to its use by taking 2 ml of essential oil to which 3 ml of DMSO was added. 1 ml of the diluted essential oil was then diluted with 3 ml of Muller-Hilton broth for a solution of 100 mg/l or 100 µg/ml, which corresponded to a concentration of 10%. The final concentrations of 0.05% to 0.5% were obtained by first diluting the 10% solution is sterile mineral water and the final dilutions in Muller-Hilton broth.

The encapsulated and nonencapsulated essential oils were tested at subinhibtory concentrations (a concentration that is immediately inferior to the effective concentration so that an eventual synergy or indifference or antagonistic association can be recognized.

The bacterial strain was placed in a Muller-Hilton broth and contacted with either the encapsulated R07 essential oil or the non encapsulated essential oil (R07) diluted as set forth above. The number of bacteria was counted at time zero (T0), 6 hours after T0(T6) and 24 hours after T0 (T24).

Example 7

Kinetic Studies of the Encapsulated Essential Oil (RO7) and Non-Encapsulated Oil (RO7) on Acinetobacter baumannii Mucoid The bacterial strain of Acinetobacter baumannii mucoid that was used was a suspension of 0.5 MF (Mac Farland) corresponding to $2 \times 10^8$ CFU (colony forming unit). The final inoculum corresponded to a dilution of $1/100^e$ of MF and thus about $2 \times 10^6$ CFU/ml.

The non encapsulated essential oil was first diluted prior to its use by taking 2 ml of essential oil to which 3 ml of DMSO was added. 1 ml of the diluted essential oil was then diluted with 3 ml of Muller-Hilton broth for a solution of 100 mg/l or 100 µg/ml, which corresponded to a concentration of 10%. The final concentrations of 0.05% to 0.5% were obtained by first diluting the 10% solution is sterile mineral water and the final dilutions in Muller-Hilton broth.

The encapsulated and nonencapsulated essential oils were tested at subinhibtory concentrations (a concentration that is immediately inferior to the effective concentration so that an eventual synergy or indifference or antagonistic association can be recognized.

The bacterial strain was in a Muller-Hilton broth and contacted with either the encapsulated R07 essential oil or the non encapsulated essential oil (R07), diluted as set forth above. The number of bacteria was measured at time zero (T0), 6 hours after T0(T6) and 24 hours after T0 (T24).

Example 8

Encapsulation of the at Least One Essential Oil and at Least One Antibiotic

The nanocapsules are prepared as in Example 1. 100 µl of an essential oil from oregano from Spain having about 63.09% of carvacrol (25 unit grams of carvacrol), an essential oil of red thyme from Spain (Thymus vulgaris) having about 47.37% thymol (8.75 unit grams of thymol), an essential oil from cloves of Madagascar (Eugenia caryophyllata) 85.19% eugenol (18.75 unit grams of eugenol), an essential oil of Sarriette from Albania having about 27.68% thymol (6.25 unit grams of thymol), an essential oil from ravintsara from Madagascar having about 55.26% eucalyptus (9.38 unit grams of eucalyptus), an essential oil from bay leaves from Croatia (*Laurus nobilis*) having about 48.56% cineole-1,8 (9.38 unit grams of cineole), an essential oil from Scotch pine having about 64.84% of alpha pinene (6.25 unit grams of alpha pinene), an essential oil from green Cajeput having about 62.11% cineole, 1-8 (6.25 unit grams of cineole) is prepared. 1 gram of meropenem and the essential oil are added to the micromulsion obtained by phase inversion in Example 1 at 45° C. at a concentration of 115 g/l.

The different suspensions were utilized alone or diluted in water or reconcentrated or lyophilized.

Example 9

Determination of the LD50 of R07 by Intraperotineal Injection for 24 Hours 25 female mice (C3H/HeN), which were 6 weeks old, were divided into 5 groups of 5 mice each. The mice each weighed about 20 g. The empty nanocapsules used in this example were prepared according to Example 1. The encapsulated R07 nanocapsules were prepared according to Example 2.

Five mice received a 100 μl intraperitoneal injection of physiologic serum as a control group.

Five mice received 12.5 mg of R07, which was formulated by diluting 100 μl of R07 in 700 μl of physiologic serum and a 100 μl of this dilution was injected intraperitoneally into each mice.

Five mice received 25 mg of R07, which was formulated by diluting 200 μl of R07 in 600 μl of physiologic serum and a 100 μl of this dilution was injected intraperitoneally into each mice.

Five mice received 50 mg of R07, which was formulated by diluting 400 μl of R07 in 400 μl of physiologic serum and a 100 μl of this dilution was injected intraperitoneally into each mice.

Five mice received 100 mg of R07, by injecting 100 μl of R07 intraperitoneally into each mice.

The R07 formulation was administered in an aqueous solution of sterile physiologic serum at a concentration of 1 g/ml. The five mice were then placed in their respective cages, which were labeled with the amounts of R07 administered and the control group. The cages were placed in a room that was temperature and humidity controlled. The mice were given food and water ad libitem.

The mortality of the mice was checked after 24 hours. The following Table I shows the results.

TABLE I

| Dose of R07 in mg | Percentage of dead mice |
|---|---|
| 0 | 0 |
| 12.5 | 0 |
| 25 | 20 |
| 50 | 60 |
| 100 | 100 |

Therefore for a 20% death rate, 1 out of 5 mice died; for a 60% death rate 3 out of 5 mice died; and for a 100% death rate 5 out of 5 mice died.

Figure 7:
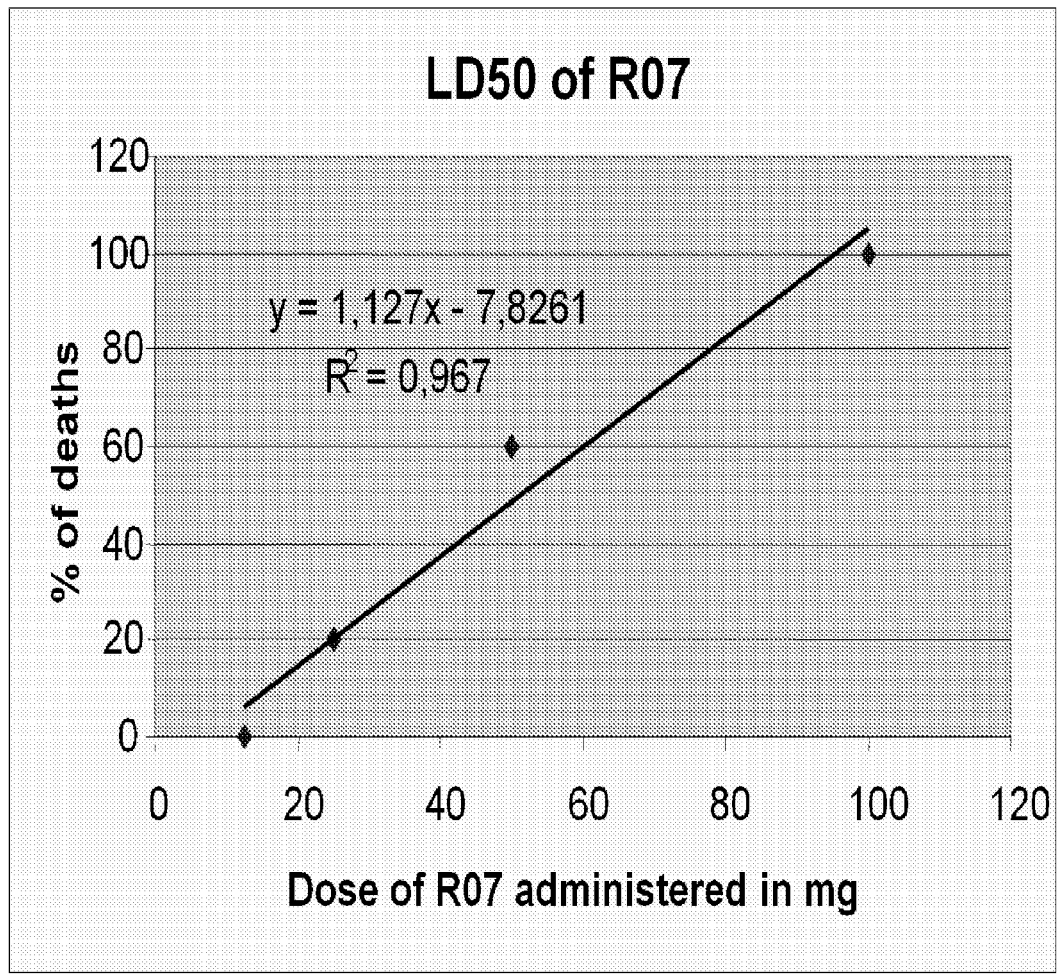
FIG. 7 is a graph illustrating the LD50% of R07 when administered to mice. As can be seen from this graph the LD50% of the administered R07 is 51.31 mg of mice weighing about 20 g and thus 2,565 mg/kg.

The percentage of deaths of the mice was then plotted versus the dose of the R07 in mg that was administered. This graph is shown in FIG. 7. Y=1.127x−7.8261 and represents the equation of the line. 1.127 is the slope of this line. Small y represents the percentage of deaths and x the dose of R07 administered in milligrams. $R^2$ represents the correlation coefficient of the line. Thus at 50% death rate x=(50+7.8261)/1.127=51.31 mg. Therefore the LD 50 for R07 is 51.31 mg and therefore 2565 mg/kg.

A comparison of R07 with other antibiotics after intraperitoneal injection of mice is set forth below in Table II. The LD 50 results were available from the literature.

TABLE II

| Antibiotics/R07 | LD50 in mice (mg/kg) by intraperitoneal injection |
|---|---|
| Piperacillin | 9970 |
| Amoxicillin | 3590 |
| R07 | 2565 |
| Ciprofloxacin | 1165 |
| Josamycin | 780 |
| Streptomycin | 525 |
| Rifampicin | 416 |
| Erythromycin | 280 |
| Gentamicin | 245 |
| Demeclocyclin | 120 |

Thus, the toxicity of R07 based on the LD 50 in comparison with other known antibiotics is: 2.2 times inferior to Ciprofloxacin, 3.3 times inferior to Josamycin, 4.9 times inferior to Streptomycin, 6.2 times inferior to Rifampicin, 9.2 times inferior to Erythromycin, 10.5 times inferior to Gentamicin and 21.4 times inferior to demeclocyclin.

The toxicity of R07 was shown to be 3.9 times higher than Piperacillin and 1.4 times higher than amoxicillin.

Example 10

Study of Nanoencapsulated R07 in Mice in a Pulmonary Model

Female mice C3H/HeN were selected to be used in this experiment due to their sensitivity with *Acinetobacter baumannii* and the reproducibility of results due to their inbreeding. The mice were rendered transiently neutropenic by an intraperitoneal injection of 150 μl of cyclophosphamide (Endoxan, 150 mg/kg) at day 4 and day 3 prior to infection. The interest in transiently making the mice immunodepressive is to permit the microorganism AYE *Acinetobacter baumannii* to be implanted in the lungs, while maintaining in the days that followed the evolution of pneumonia with granulocytes. The influx of granulocytes were produced at day 2.

The inoculation of AYE *Acinetobacter baumannii* was performed intratracheally using an intubation tube in mice that were briefly anesthesized with isoflurane under a pressure of 3 for the oxygen and 0.5 to 1 for the isoflurane. Once the mice were asleep the tube was introduced intratracheally. It was further verified that the test ring of the tube was well positioned in the trachea and not the eosophagus. The AYE *Acinetobacter baumannii* was administered in a suspension of $5\times10^6$ CFU (colony-forming units) in 50 μl of physiologic serum. The mice were then placed in cages in groups of a maximum of 5 animals per cage. The cages were placed in a room that was temperature and humidity controlled. The mice were given food and water ad libitem.

The survival of the mice were evaluated for 5 days and clinical criteria of the mice such as their weight, fur, mobility and the presence or absence of conjunctivitis was also undertaken.

The empty nanocapsules were prepared according to Example 1. The encapsulated R07 nanocapsules were prepared according to Example 2. Both the empty nanocapsules and the encapsulated R07 nanocapsules were diluted in sterile physiologic serum prior to administration to the mice.

The concentration of encapsulated R07 in the nanocapsules was 20 mg/ml. For a mouse of 20 g this corresponds to 0.4 mg of R07 per mouse per day.

The treatment was administered for 3 days to 40 mice which were randomized and divided into 8 groups as follows:

Group 1—5 mice received 3 intraperitoneal injections of physiological serum at 4 hour intervals. Therefore, 200 μl of sterile physiologic serum was injected 3 times a day to each of the 5 mice in Group 1.

Group 2—5 mice received 3 intraperitoneal injections of empty nanocapsules lacking an active principle at 4 hour intervals at a concentration of 12 mg/day.
Therefore, 200 μl of empty nanocapsules at 20 mg/ml was injected 3 times a day to each of the 5 mice in Group 2.

Group 3—5 mice received intraperitoneal injections of encapsulated R07 at 4 hour intervals at a concentration of 12 mg/day. Therefore, 200 μl of encapsulated R07 nanocapsules at 20 mg/ml was injected 3 times a day to each of the 5 mice in Group 3.

Group 4—5 mice received intraperitoneal injections of encapsulated R07 at 4 hour intervals at a concentration of 6 mg/day. Therefore, 4 ml of encapsulated R07 nanocapsules at 20 mg/ml were added to 4 ml of sterile physiologic serum and 200 μl were injected 3 times a day to each of the 5 mice in Group 4.

Group 5—5 mice received intraperitoneal injections of encapsulated R07 at 4 hour intervals at a concentration of 3 mg/day. Therefore, 4 ml of encapsulated R07 nanocapsules at 10 mg/ml were added to 4 ml of sterile physiologic serum and 200 μl were injected 3 times a day to each of the 5 mice in Group 5.

Group 6—5 mice received intraperitoneal injections of encapsulated R07 at 4 hour intervals at a concentration of 1.5 mg/day. Therefore, 4 ml of encapsulated R07 nanocapsules at 5 mg/ml were added to 4 ml of sterile physiologic serum and 200 μl were injected 3 times a day to each of the 5 mice in Group 6.

Group 7—5 mice received intraperitoneal injections of encapsulated R07 at 4 hour intervals at a concentration of 0.75 mg/day. Therefore, 4 ml of encapsulated R07 nanocapsules at 2.5 mg/ml were added to 4 ml of sterile physiologic serum and 200 μl were injected 3 times a day to each of the 5 mice in Group 7.

Group 8—5 mice received intraperitoneal injections of encapsulated R07 at 4 hour intervals at a concentration of 0.375 mg/day. Therefore, 4 ml of encapsulated R07 nanocapsules at 1.25 mg/ml were added to 4 ml of sterile physiologic serum and 200 μl were injected 3 times a day to each of the 5 mice in Group 8.

Clinical evaluations of the mice in each group were recorded during 5 days. The clinical evaluations that were performed were the weight of each mouse, the condition of the fur, the mobility and the presence or absence of conjunctivitis. The following rating system was used:

| For the condition of the fur: | 0 = normal fur, smooth |
| --- | --- |
| | 1 = covered with coarse stiff hair, greasy |
| For the mobility: | 0 = mobility that is normal and spontaneous |
| | 1 = mobility after stimulation |
| | 2 = no mobility |
| For conjunctivitis | 0 = absence of conjunctivitis |
| | 1 = presence of conjunctivitis |

The sum of the above items having a maximum score of 4 reflects that state of health of each mouse. A score of 0 reflects good health.

The mice were checked in the morning and night to see if any mouse died and dead mice were removed from the cage.

The results obtained are set forth in Table III below.

TABLE III

| Control Physiologic Serum | | | | | | |
| --- | --- | --- | --- | --- | --- | --- |
| Group 1 | | Day 0 | Day 1 | Day 2 | Day 3 | Day 4 |
| mouse 1 | weight (g) | 19.6 | 16.31 | x | x | x |
| | clinical evaluation score | 0 | 3 | x | x | x |
| | mortality | no | no | dead | x | x |
| mouse 2 | weight (g) | 19.6 | 16.65 | 15.74 | x | x |
| | clinical evaluation score | 0 | 3 | 3 | x | x |
| | mortality | no | No | non | dead | x |
| mouse 3 | weight (g) | 18.8 | 15.93 | x | x | x |
| | clinical evaluation score | 0 | 3 | x | x | x |
| | mortality | no | no | dead | x | x |
| mouse 4 | weight (g) | 19.6 | 16.25 | 15.9 | x | x |
| | clinical evaluation score | 0 | 3 | 3 | x | x |
| | mortality | no | no | no | dead | x |
| mouse 5 | weight (g) | 19.4 | 16.92 | x | x | x |
| | clinical evaluation score | 0 | 3 | x | x | x |
| | mortality | no | no | dead | x | x |

| empty nanocapsules: 12 mg/mouse/day | | | | | | |
| --- | --- | --- | --- | --- | --- | --- |
| Group 2 | | Day 0 | Day 1 | Day 2 | Day 3 | Day 4 |
| mouse 1 | weight (g) | 19 | 16.22 | 14.96 | x | x |
| | clinical evaluation score | 0 | 1 | 3 | x | x |
| | mortality | no | no | no | dead | x |
| mouse 2 | weight (g) | 19.42 | 16.33 | 15.1 | 15.05 | 14.52 |
| | clinical evaluation score | 0 | 3 | 1 | 2 | 3 |
| | mortality | no | no | no | no | no |
| mouse 3 | weight (g) | 19.2 | 17.2 | 15.24 | x | x |
| | clinical evaluation score | 0 | 3 | 3 | x | x |
| | mortality | no | no | no | dead | x |
| mouse 4 | weight (g) | 18.2 | 16.62 | 14.03 | 13.84 | x |
| | clinical evaluation score | 0 | 1 | 3 | 4 | x |
| | mortality | no | no | no | no | dead |
| mouse 5 | weight (g) | 20 | 15.04 | 16.37 | x | x |
| | clinical evaluation score | 0 | 1 | 1 | x | x |
| | mortality | no | no | no | dead | x |

TABLE III-continued encapsulated R07 nanoencapsule: 12 mg/mouse/day

| Group 3 | | Day 0 | Day 1 | Day 2 | Day 3 | Day 4 |
|---|---|---|---|---|---|---|
| mouse 1 | weight (g) | 19.4 | 15.95 | x | x | x |
| | clinical evaluation score | 0 | 1 | x | x | x |
| | mortality | no | no | dead | x | x |
| mouse 2 | weight (g) | 19.6 | x | x | x | x |
| | clinical evaluation score | 0 | x | x | x | x |
| | mortality | no | dead | x | x | x |
| mouse 3 | weight (g) | 20.2 | 17.58 | x | x | x |
| | clinical evaluation score | 0 | 1 | x | x | x |
| | mortality | no | no | dead | x | x |
| mouse 4 | weight (g) | 18.8 | 15.98 | x | x | x |
| | clinical evaluation score | 0 | 1 | x | x | x |
| | mortality | no | no | dead | x | x |
| mouse 5 | weight (g) | 19.6 | 17.14 | x | x | x |
| | clinical evaluation score | 0 | 2 | x | x | x |
| | mortality | no | no | dead | x | x | encapsulated R07 nanoencapsule: 6 mg/mouse/day

| Group 4 | | Day 0 | Day 1 | Day 2 | Day 3 | Day 4 |
|---|---|---|---|---|---|---|
| mouse 1 | weight (g) | 20.8 | 17.59 | 16.61 | x | x |
| | clinical evaluation score | 0 | 2 | 2 | x | x |
| | mortality | no | no | no | dead | |
| mouse 2 | weight (g) | 20.2 | 17.39 | 16.39 | x | x |
| | clinical evaluation score | 0 | 1 | 2 | x | x |
| | mortality | no | no | no | dead | x |
| mouse 3 | weight (g) | 20.2 | 17.38 | x | x | x |
| | clinical evaluation score | 0 | 3 | x | x | x |
| | mortality | no | no | dead | x | x |
| mouse 4 | weight (g) | 19.2 | 16.47 | 15.7 | x | x |
| | clinical evaluation score | 0 | 1 | 3 | x | x |
| | mortality | no | no | no | dead | x |
| mouse 5 | weight (g) | 19.8 | 17.2 | 17.11 | 18.34 | 19.48 |
| | clinical evaluation score | 0 | 0 | 0 | 0 | 0 |
| | mortality | no | no | no | no | no | encapsulated R07 nanoencapsule: 3 mg/mouse/day

| Group 5 | | Day 0 | Day 1 | Day 2 | Day 3 | Day 4 |
|---|---|---|---|---|---|---|
| mouse 1 | weight (g) | 19.8 | 16.79 | 15.43 | 15.26 | 14.78 |
| | clinical evaluation score | 0 | 2 | 2 | 2 | 2 |
| | mortality | no | no | no | no | no |
| mouse 2 | weight (g) | 18.6 | 15.76 | 14.76 | x | x |
| | clinical evaluation score | 0 | 2 | 3 | x | x |
| | mortality | no | no | no | dead | x |
| mouse 3 | weight (g) | 18.6 | 15.41 | x | x | x |
| | clinical evaluation score | 0 | 1 | x | x | x |
| | mortality | no | no | dead | x | x |
| mouse 4 | weight (g) | 19.4 | 16.79 | x | x | x |
| | clinical evaluation score | 0 | 2 | x | x | x |
| | mortality | no | no | dead | x | x |
| mouse 5 | weight (g) | 20.6 | 17.7 | 16.71 | 16.4 | 15.92 |
| | clinical evaluation score | 0 | 2 | 2 | 2 | 2 |
| | mortality | no | no | no | no | no | encapsulated R07 nanoencapsule: 1.5 mg/mouse/day

| Group 6 | | Day 0 | Day 1 | Day 2 | Day 3 | Day 4 |
|---|---|---|---|---|---|---|
| mouse 1 | weight (g) | 18.8 | 15.53 | 14.59 | 14.05 | 13.41 |
| | clinical evaluation score | 0 | 2 | 2 | 2 | 2 |
| | mortality | no | no | no | no | no |
| mouse 2 | weight (g) | 20.2 | 17.55 | 16.32 | 14.31 | x |
| | clinical evaluation score | 0 | 1 | 1 | 2 | x |
| | mortality | no | no | no | no | dead |
| mouse 3 | weight (g) | 19 | 16.34 | 14.78 | 17 | 17.17 |
| | clinical evaluation score | 0 | 2 | 1 | 0 | 0 |
| | mortality | no | no | no | no | no |
| mouse 4 | weight (g) | 20 | 17.18 | 16.04 | x | x |
| | clinical evaluation score | 0 | 1 | 3 | x | x |
| | mortality | no | no | no | dead | x |
| mouse 5 | weight (g) | 21 | 18.1 | 16.83 | x | x |
| | clinical evaluation score | 0 | 2 | 0 | x | x |
| | mortality | no | no | no | dead | x | encapsulated R07 nanoencapsule: 0.75 mg/mouse/day

| Group 7 | | Day 0 | Day 1 | Day 2 | Day 3 | Day 4 |
|---|---|---|---|---|---|---|
| mouse 1 | weight (g) | 19.6 | 17.23 | 15.45 | 14.95 | 14.97 |
| | clinical evaluation score | 0 | 1 | 1 | 2 | 2 |
| | mortality | no | no | no | no | no |
| mouse 2 | weight (g) | 20.2 | 17.45 | 15.84 | 15.13 | 14.44 |
| | clinical evaluation score | 0 | 3 | 2 | 1 | 1 |
| | mortality | no | no | no | no | no |
| mouse 3 | weight (g) | 19.8 | 17.18 | 15.46 | 15.21 | 15.47 |
| | clinical evaluation score | 0 | 2 | 2 | 1 | 1 |
| | mortality | no | no | no | no | no |
| mouse 4 | weight (g) | 20.2 | 17.47 | 16.1 | 15.43 | 14.9 |
| | clinical evaluation score | 0 | 1 | 1 | 1 | 1 |
| | mortalité | no | no | no | no | no |
| mouse 5 | weight (g) | 19.6 | 17.34 | 16.11 | x | x |
| | clinical evaluation score | 0 | 2 | 1 | x | x |
| | mortality | no | no | no | dead | x | encapsulated R07 nanoencapsule: 0.375 mg/mouse/day

| Group 8 | | Day 0 | Day 1 | Day 2 | Day 3 | Day 4 |
|---|---|---|---|---|---|---|
| mouse 1 | weight (g) | 19.2 | 15.88 | 14.85 | 14.07 | 13.66 |
| | clinical evaluation score | 0 | 1 | 2 | 1 | 3 |
| | mortality | no | no | no | no | no |

TABLE III-continued

| mouse 2 | weight (g) | 19.6 | 16.65 | 15.35 | x | x |
|---|---|---|---|---|---|---|
| | clinical evaluation score | 0 | 1 | 1 | x | x |
| | mortality | no | no | no | dead | x |
| mouse 3 | weight (g) | 19.2 | 16.53 | 15.2 | x | x |
| | clinical evaluation score | 0 | 3 | 2 | x | x |
| | mortality | no | no | no | dead | x |
| mouse 4 | weight (g) | 18.4 | 15.94 | x | x | x |
| | clinical evaluation score | 0 | 1 | x | x | x |
| | mortality | no | no | dead | x | x |
| mouse 5 | weight (g) | 20.4 | 17.12 | 15.95 | 15.47 | x |
| | clinical evaluation score | 0 | 2 | 3 | 4 | x |
| | mortality | no | no | no | no | dead |

Weight Loss

The results set forth in this example illustrate that there is an important loss of weight at day 1 for all of the mice of an average of 3 grams, which is 15% of their total weight. At day 2 the mice continued to lose weight on the average of 1 gram. Only mouse 5 that was administered 6 mg of encapasulated R07 nanocapsules regained weight beginning at day 4. For the other mice at day 4 the weight was stabilized, but there was no regaining of weight.

Figure 8:
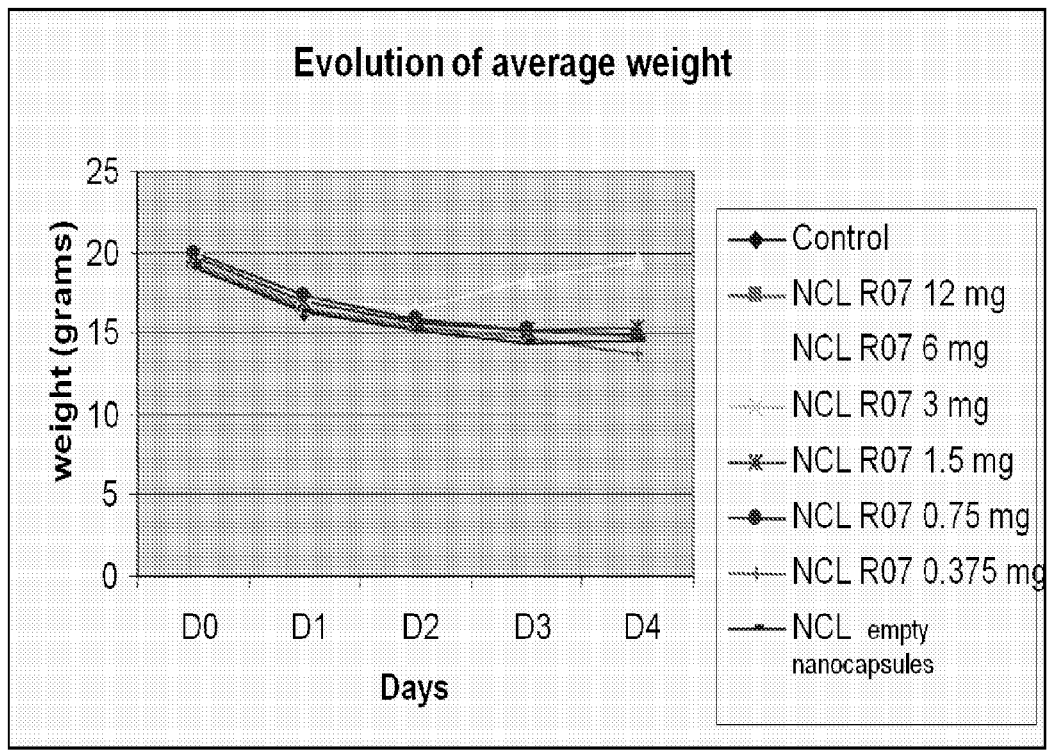
FIG. 8 is a bar graph illustrating the amount of weight loss in mice infected with *Acinetobacter baumannii* that were administered empty and encapsulated nanocapsules (NCL) at various concentrations ranging from 0.375 mg of encapsulated R07 to 12 mg of encapsulated R07 over a four day period.

FIG. 8 shows the evolution of the average weight for each group.

Clinical Evaluation Scores

Figure 9A:
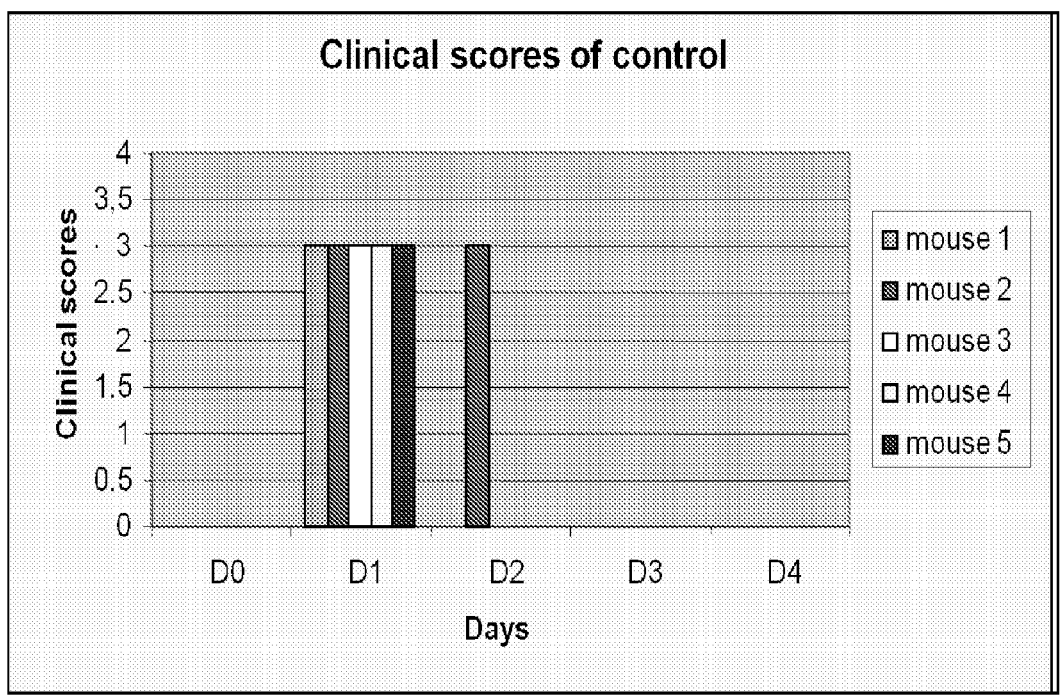
FIG. 9A is the control.
Figure 9B:
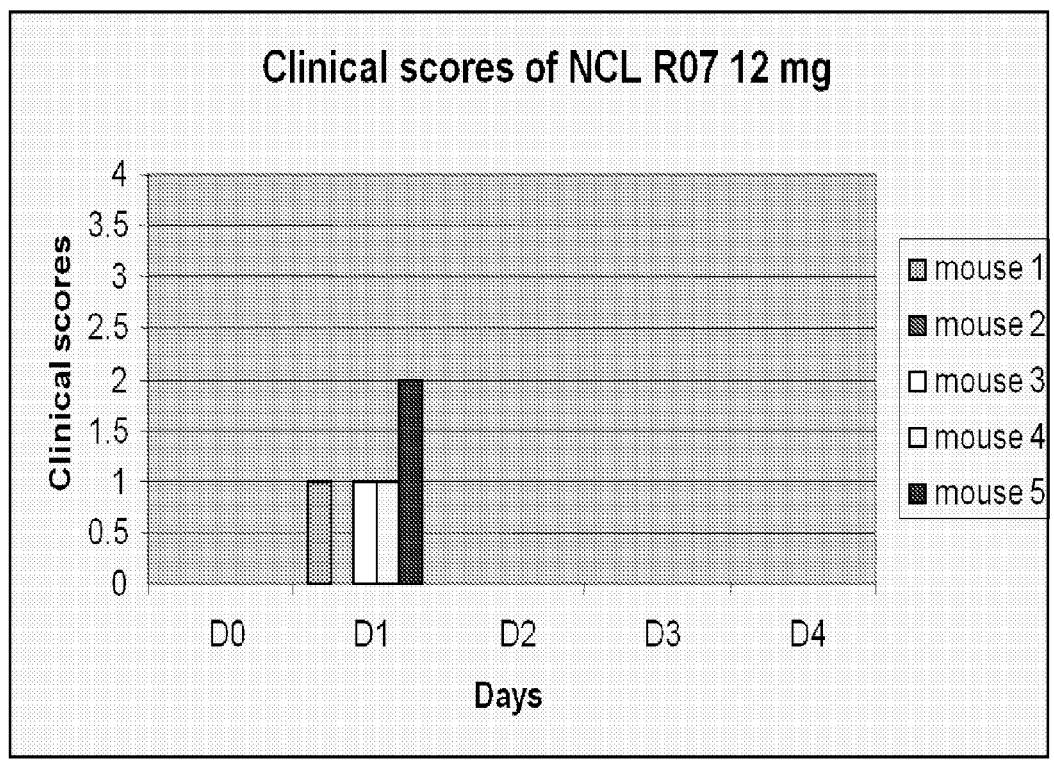
FIG. 9B are the clinical results when mice were administered 12 mg of encapsulated R07 nanocapsulels (NCL) and FIG. 9C are the clinical results when mice were administered 6 mg of encapsulated R07 nanocapsules (NCL).
Figure 9C:
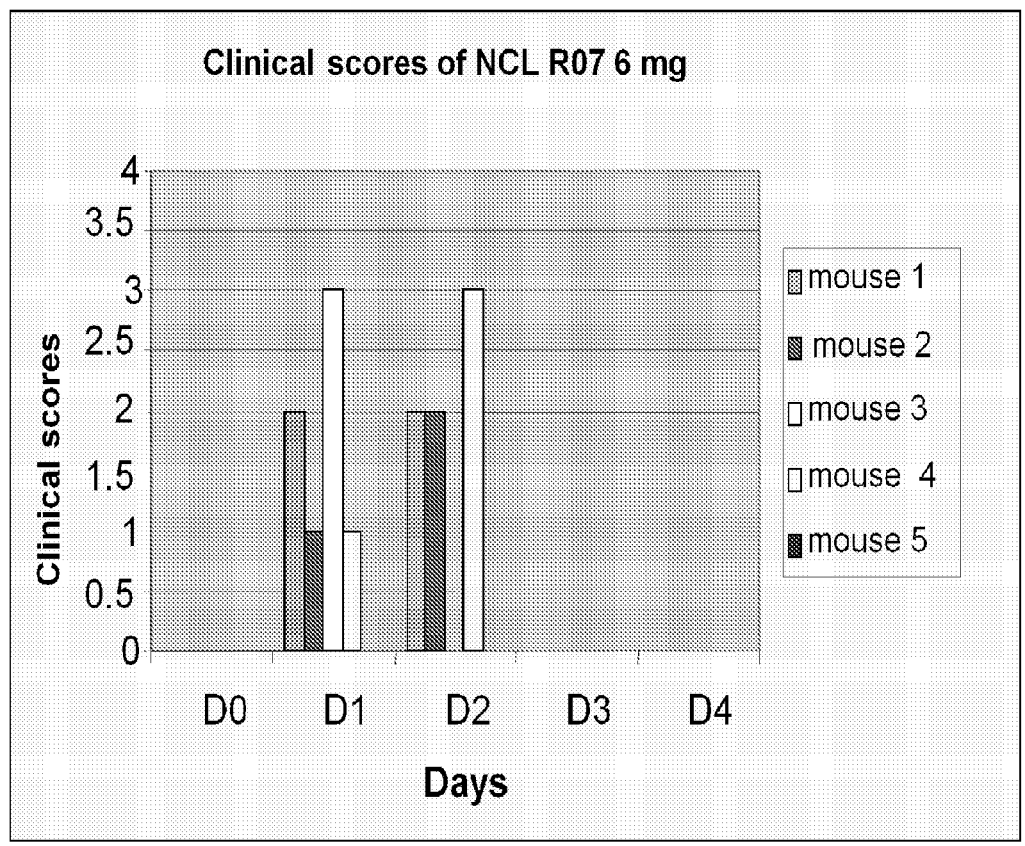
Figure 10A:
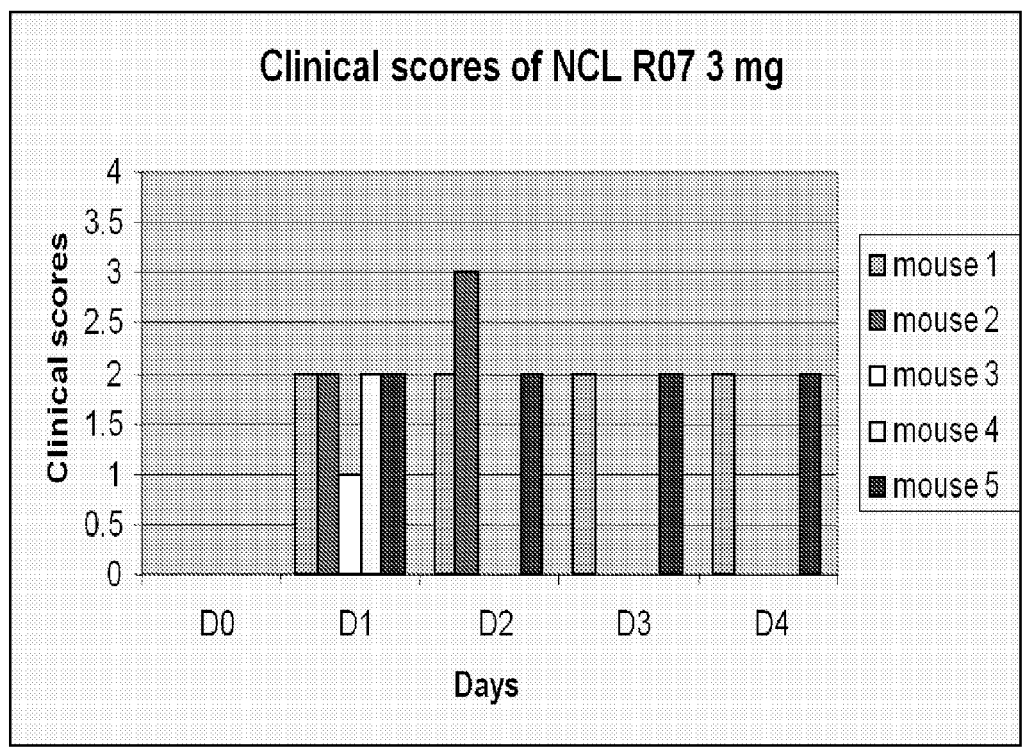
FIG. 10 are bar graphs of various clinical studies of mice infected with *Acinetobacter baumannii* that were administered encapsulated nanocapsules at various concentrations over a four day period.
Figure 10B:
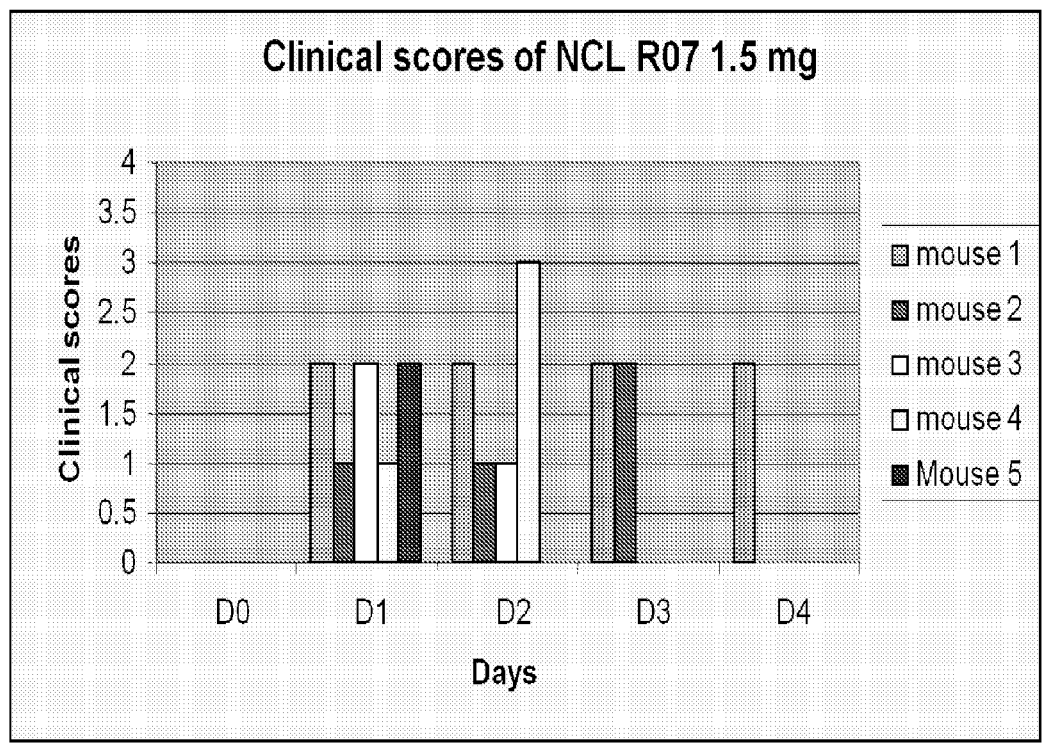
Figure 10C:
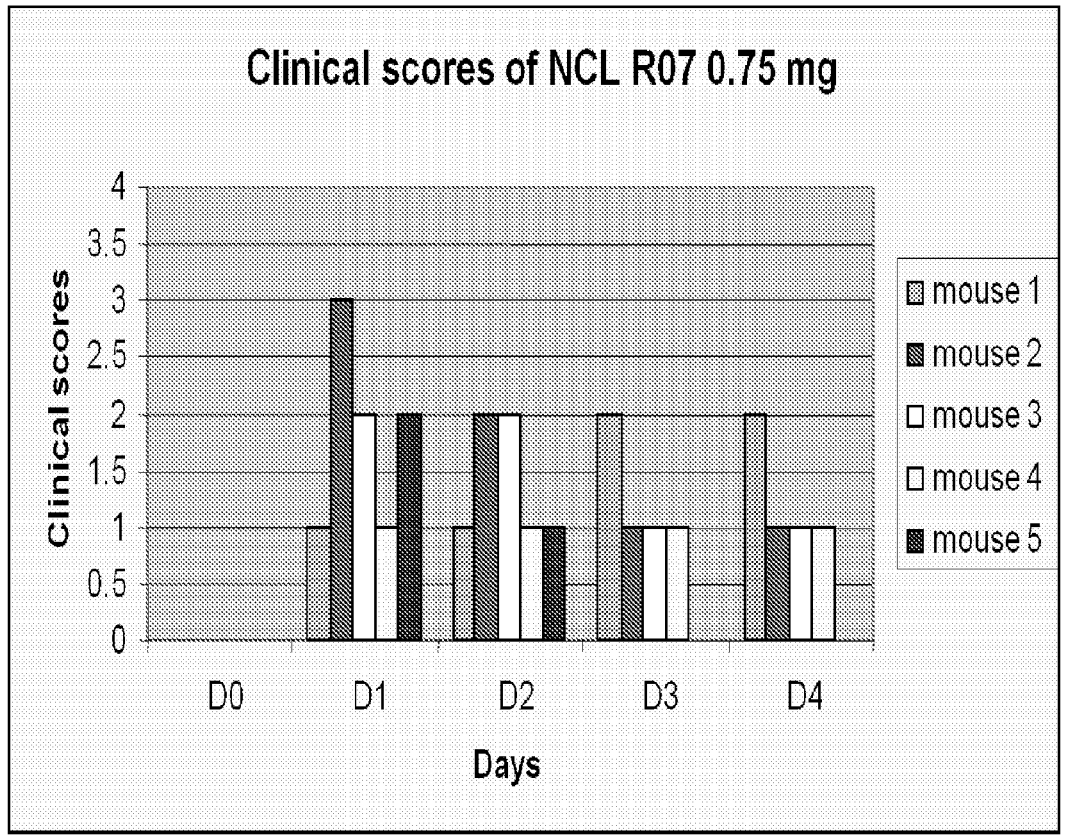
Figure 11A:
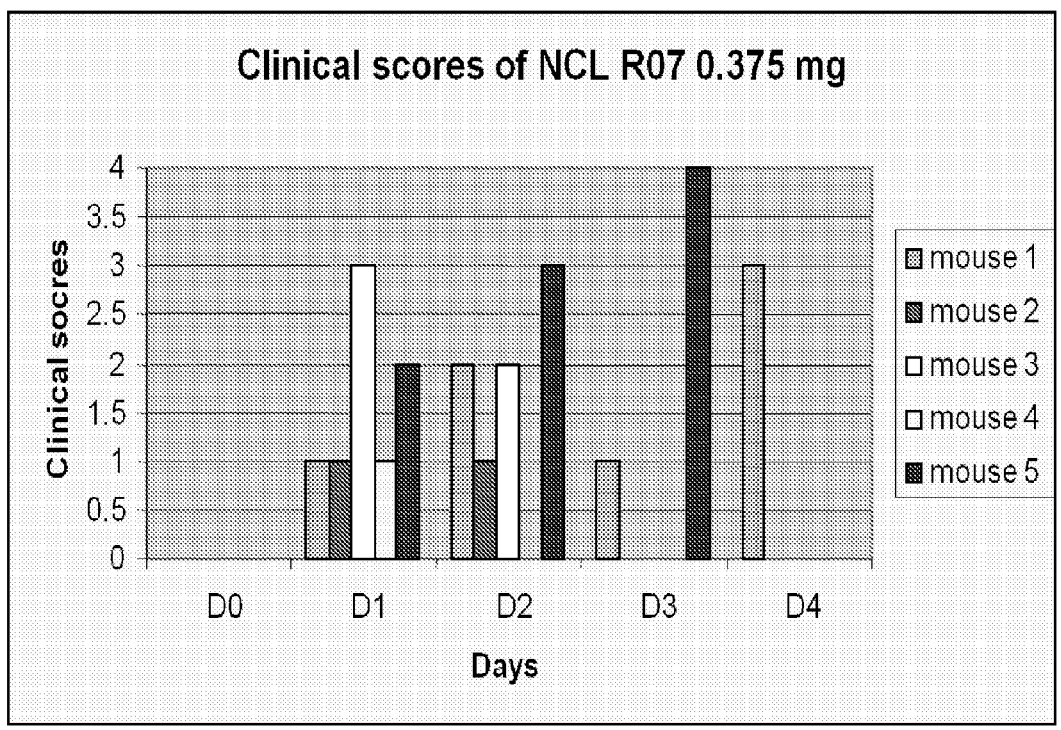
FIG. 11A are the clinical results when mice were administered 0.375 mg of encapsulated R07 nanocapsulels (NCL) and FIG. 11B are the clinical results when mice were administered empty nanocapsules.
Figure 11B:
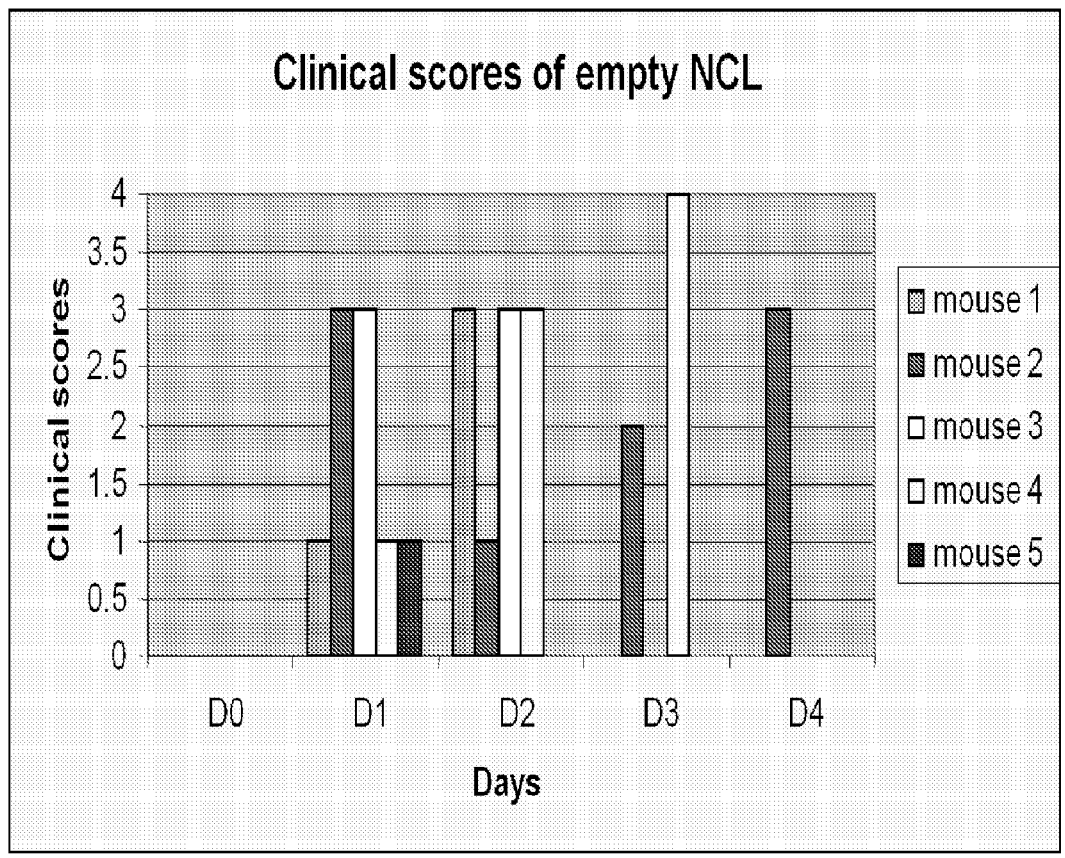
FIG. 11 are bar graphs of various clinical studies of mice infected with *Acinetobacter baumannii* that were administered empty and encapsulated nanocapsules at various concentrations over a four day period.

The results are shown in FIGS. 9 to 11.

The clinical evaluation scores had an average score of 3 for the controls and the empty nanocapsules. The lowest scores were obtained for the groups that were administered the encapsulated R07 at 0.75 my and 1.5 mg.

Percentage Mortality

The percentage mortality is shown in the following Table IV.

TABLE IV

| | Control | 12 mg NCL* R07 | 6 mg NCL* R07 | 3 mg NCL* R07 | 1.5 mg NCL* R07 | 0.75 mg NCL* R07 | 0.375 mg NCL* R07 | empty nanocapsules |
|---|---|---|---|---|---|---|---|---|
| Day 0 | 5 | 5 | 5 | 5 | 5 | 5 | 5 | 5 |
| Day 1 | 5 | 4 | 5 | 5 | 5 | 5 | 5 | 5 |
| Day 2 | 2 | 0 | 4 | 3 | 5 | 5 | 4 | 4 |
| Day 3 | 0 | 0 | 1 | 2 | 2 | 4 | 1 | 2 |
| Day 4 | 0 | 0 | 1 | 2 | 2 | 4 | 1 | 1 |

NCL* is an abbreviation for the encapsulated R07 nanocapsules

Figure 12:
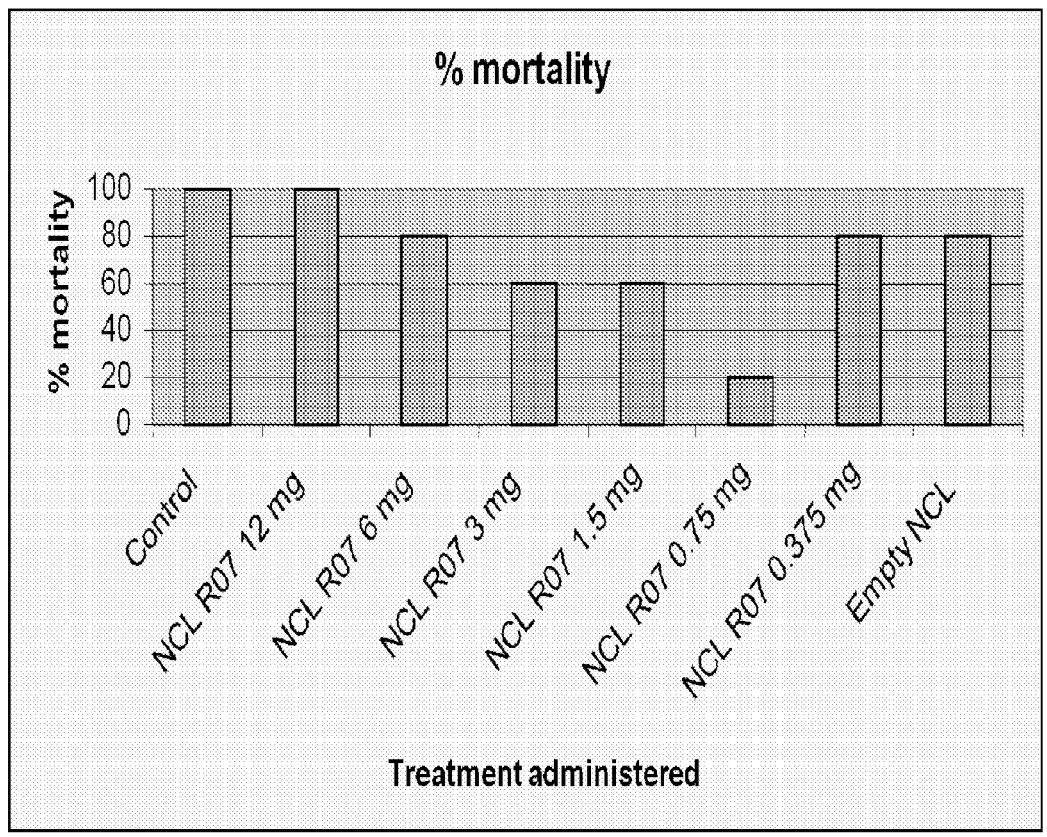
FIG. 12 is a bar graph illustrating the percentage mortality when mice were administered various amounts of encapsulated R07 nanocapsules (NCL) and empty nanocapsules.
Figure 13:
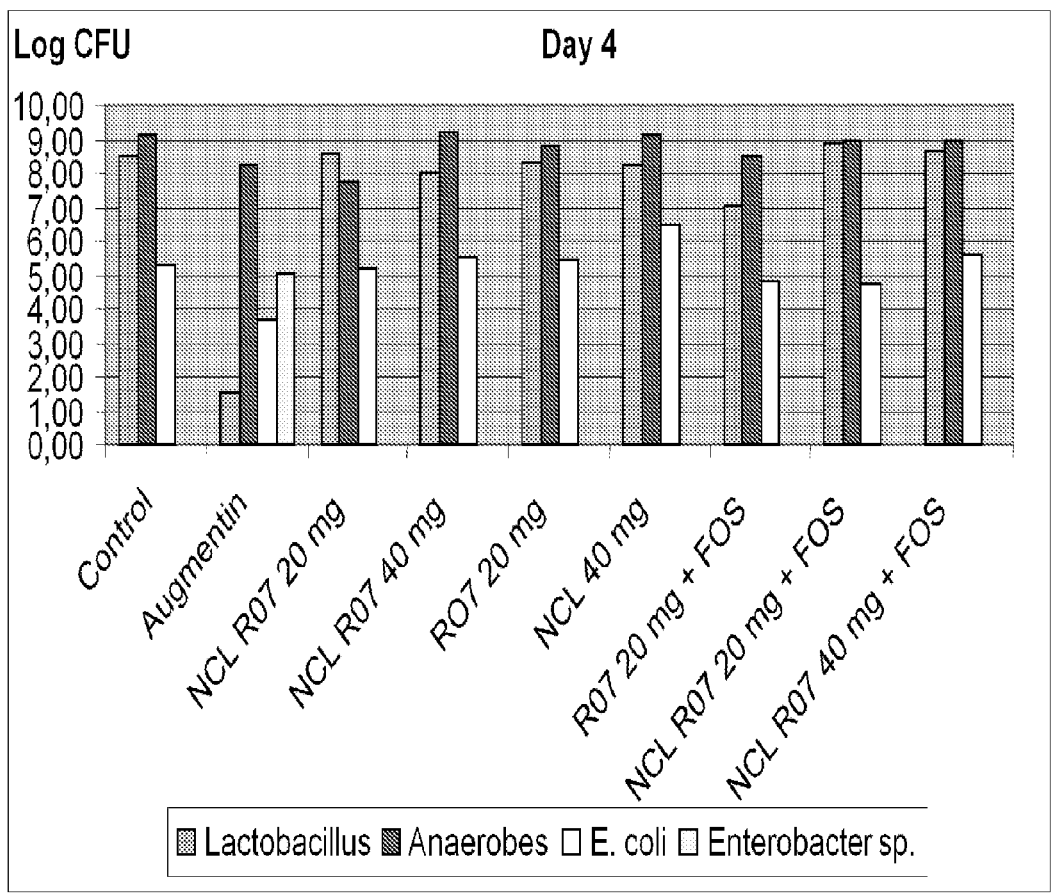
FIG. 13 is a bar graph illustrating the amount of colony forming units (CFU) of *Lactobacillus, Anaerobic* bacteria, *E. coli* and Enterobacteria present in the stools of mice at day 4 when administered AMC (Augmentin) various concentrations of encapsulated R07 nanocapsules, empty nanocapsules, R07 and fructo-oligosaccharieds (FOS) and various concentrations of encapsulated R07 nanocapsules and fructo-oligosaccharides (FOS).
Figure 14:
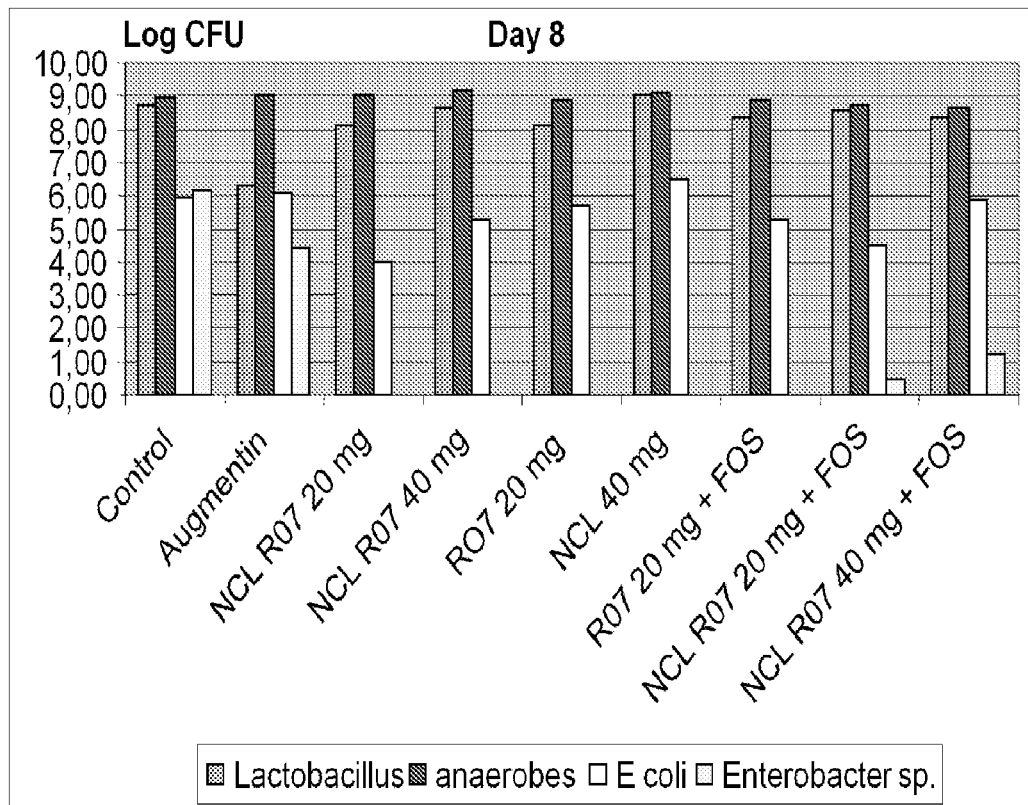
FIG. 14 is a bar graph illustrating the amount of colony forming units (CFU) of *Lactobacillus*, anaerobic bacteria, *E. coli* and Enterobacteria present in the stools of mice at day 8 when administered AMC (Augmentin®) various concentrations of encapsulated R07 nanocapsules, empty nanocapsules, R07 and fructo-oligosaccharieds (FOS) and various concentrations of encapsulated R07 nanocapsules and fructo-oligosaccharides (FOS).

A bar graph of the percentage mortality for each group is shown in FIG. 12. The highest mortality rate was in the control group and Group 3 where 12 mg of encapsulated R07 nancapsules were administered with 100% mortality at day 2.

For Groups 2, 4 and 8 a mortality of 80% was observed at day 5. For Groups 5 and 6 the mortality was 60%. The lowest mortality is observed in Group 7 where 20% was observed.

The dose of encapsulated R07 nanocapsules at 0.75 mg/mouse/day administered for 3 days to Group 7 permitted to maintain living 80% of the population of 5 mice. With the exception of Group 3, which was administered 12 mg/mouse/day, the mortality rates of the mice treated with the encapsulated R07 nanocapsules survived longer than the control Group 1.

Example 11

The Evaluation of the impact of R07 and encapsulated R07 Nanocapsules, a Combination of Amoxicillin and Clavulanic Acid and a Fructo-Oligosaccharide on the Digestive Commensal Flora in Mice Forty-five, 3 month old female Swiss mice, were randomized and divided into 9 groups of 5 per cage. The cages in this example were placed in a room that was temperature and humidity controlled. The mice were given food and water ad libitem.

Each mouse in the 9 groups received the following:

Group 1—control—100 µl of physiologic serum was administered by gavage, 3 times a day, thus 300 µl per day.

Group 2 was administered by gavage, 3 times a day 100 µl of amoxicillin and clavulanic acid (Augmentin) at 1.4 mg/ml that corresponds to a dosage of 0.75 mg per day for a 20 g mouse.

Group 3 was administered by gavage, 3 times a day 100 µl of R07 alone at 1.4 mg/ml that corresponds to a dose of 0.4 mg/mouse/day.

Group 4 was administered by gavage, 3 times a day 100 µl of encapsulated R07 nanocapsules at 1.4 mg/ml that corresponds to a dose of 0.4 mg/mouse/day.

Group 5 was administered by gavage, 3 times a day 100 µl of encapsulated R07 nanocapsules at 2.8 mg/ml that corresponds to a dose of 0.8 mg/mouse/day.

Group 6 was administered by gavage, 3 times a day 100 µl of empty nanocapsules at 2.8 mg/ml.

Group 7 was administered by gavage, 3 times a day 100 µl of a solution of R07 at 1.4 mg/ml and fructo-olgisachharide at 8.6 mg/ml.

Group 8 was administered by gavage, 3 times a day 100 µl of a solution of encapsulated R07 nanocapsules at 1.4 mg/ml and fructo-olgisachharide at 8.6 mg/ml.

Group 9 was administered by gavage, 3 times a day 100 µl of a solution of R07 at 2.8 mg/ml and fructo-olgisachharide at 8.6 mg/ml.

The administration of the above took place at 4 hour intervals for 5 days at day 0 until day 4.

The stools of each mouse were collected in the morning of days 1 to 4 before the first gavage with sterile tweezers, placed in sterile Eppendorf tubes, weighed and stored at −80° C. for later analysis. The stools were also collected at day 8, 4 days after the final gavage.

The mice were euthanized with $CO_2$ at the end of the experiment.

Identification of the Number and Type of Germs Present in the Flora of the Digestive Tract of the Mice The droppings were unfrozen at room temperature. Each of the droppings was weighed, diluted in distilled water and homogenized. If the weight was ≤0.050 g than 1 ml of distilled water was used. If the weight was ≤0.100 g than 5 ml of distilled water was used. If the weight was ≥0.100 g than 10 ml of distilled water was used to obtain a dilution of $10^{-1}$ for all weights. Dilutions of $10^{-3}$ and $10^{-5}$ were also undertaken.

100 µl of each dilution were streaked onto 3 different types of agar; blood agar (BA), an agar that contains antibiotic inhibitors that permits the selection of Gram positive bacteria (CNA) and an agar that is a chromogenic urinary tract infection (UTI) agar.

After streaking each sample onto the agar the blood agar and the UTI agar plates were incubated in a microbiological incubator at 37° C. for 24 hours under aerobic conditions. The ANC and BA plates were incubated in a microbiological incubator at 37° C. for 48 hours under aerobic and anaerobic conditions in a deoxygenated jar. The isolation of different colonies that grew under aerobic conditions was performed on blood agar plates.

The coloration of the colonies permitted to identify whether the bacteria were gram positive or gram negative and to indicate their morphology. A test for catalase was effectuated to differentiate *Staphyloccocus* from *Streptococcus* and a test for oxidase was effectuated for the gram negative bacteria, which guided the choice of identification system. The method of Vitek 2 (galleries with an automatic reading) was used to identify the majority of bacteria. It was necessary to identify other bacteria by using the biochemical manual method of API galleries.

Therefore a gram negative non-Enterobacteria was identified using an API20NE gallery, Enterobacteria was identified using an API 20E gallery. *Bacillus* sp. were identified using an API 20E gallery and an API 50CHB gallery.

The results are set forth in Table V and VI below. Table V is a comparison of the average values obtained in log 10 at day 4 and day 8 based on the administered product compared to the control of the dominant flora. Table VI is a comparison of average values in log 10 and the standard deviation (SD) obtained at day 4 and day 8 based on the administered product compared to the control for the dominant flora of enterobacteria.

TABLE V

| | LACTOBACILLES | | | | | | ANAEROBES | | | | | |
|---|---|---|---|---|---|---|---|---|---|---|---|---|
| | Day 4 | | | Day 8 | | | Day 4 | | | Day 8 | | |
| | Mean | SD | t | Mean | SD | t | Mean | SD | t | Mean | SD | t |
| Control | 8.52 | 0.31 | | 8.69 | 0.390 | | 9.090 | 0.160 | | 8.920 | 0.147 | — |
| AMC (Augmentin) | 1.54 | 3.08 | 4.89* | 6.30 | 4.20 | 0.42 | 8.230 | 2.200 | 0.50 | 8.990 | 0.164 | 0.50 |
| NCL R07 20 mg | 8.55 | 2.68 | 0.110 | 8.13 | 0.36 | 0.71 | 7.750 | 2.60 | 0.76 | 8.990 | 0.120 | 1.02 |
| NCL R07 40 mg | 8.04 | 1.29 | 0.976 | 8.63 | 0.40 | 0.19 | 9.240 | 0.270 | 0.96 | 9.170 | 0.220 | 1.90 |
| R07 20 mg | 8.30 | 0.38 | 1.400 | 8.12 | 0.25 | 2.5* | 8.820 | 0.420 | 1.16 | 8.860 | 0.370 | 0.31 |
| NCL 40 mg | 8.27 | 1.00 | 0.730 | 9.02 | 0.20 | 2.2* | 9.130 | 0.340 | 0.32 | 9.130 | 0.200 | 1.45 |
| R07 20 mg + FOS | 7.08 | 2.00 | 2.08* | 8.32 | 0.64 | 1.49 | 8.510 | 0.330 | 3.0* | 8.850 | 0.080 | 0.90 |
| NCL R07 20 mg + FOS | 8.85 | 0.53 | 0.490 | 8.56 | 0.34 | 0.63 | 8.980 | 0.360 | 0.60 | 8.690 | 0.120 | 2.10 |
| NCL R07 40 mg + FOS | 8.68 | 0.81 | 0.520 | 8.34 | 0.77 | 1.26 | 8.930 | 0.400 | 0.71 | 8.670 | 0.530 | 0.21 |

*indicates that the student T test is significant for T > 2

TABLE VI

| | E. coli | | | | Enterobacter sp. | | | |
|---|---|---|---|---|---|---|---|---|
| | Day 4 | | Day 8 | | Day 4 | | Day 8 | |
| | Mean | SD | Mean | SD | Mean | SD | Mean | SD |
| Control | 5.25 | 0.45 | 5.95 | 1.68 | 0.00 | 0.00 | 6.20 | 1.40 |
| AMC (Augmentin) | 3.70 | 3.97 | 6.10 | 1.32 | 5.05 | | 4.41 | 4.28 |
| NCL R07 20 mg | 5.20 | 0.67 | 3.95 | 2.20 | 0.00 | 0.00 | 0.00 | 0.00 |
| NCL R07 40 mg | 5.56 | 1.59 | 5.30 | 2.00 | 0.00 | 0.00 | 0.00 | 0.00 |
| RO7 20 mg | 5.47 | 1.10 | 5.72 | 0.66 | 0.00 | 0.00 | 0.00 | 0.00 |
| NCL 40 mg | 6.50 | 0.70 | 6.50 | 1.80 | 0.00 | 0.00 | 0.00 | 0.00 |
| R07 20 mg + FOS | 4.80 | 1.80 | 5.23 | 0.36 | 0.00 | 0.00 | 0.00 | 0.00 |
| NCL R07 20 mg + FOS | 4.70 | 0.63 | 4.50 | 1.15 | 0.00 | 0.00 | 0.48 | 1.50 |
| NCL R07 40 mg + FOS | 5.59 | 0.70 | 5.87 | 1.20 | 0.00 | 0.00 | 1.20 | 2.50 |

From these experiments it was determined that the control group had predominantly *lactobacillus* and anaerobes bacteria which were present in an amount between $10^8$ and $10^{10}$ bacteria per gram stool. Enterobacteria, Enterococci and Streptococci had between $10^5$ and $10^7$ bacteria per gram of stool. However there was an increase in 2 logs of Enterobacteria on day 8.

The predominant species of the Enterobacteria in the control group was *Escherichia coli*, the predominant species of the Staphylococci was *Staphylococcus xylosus* and the species predominant for *Bacillus* was *Bacillus cereus*.

The R07 at 20 mg/kg/day group had predominantly *Lactobacillus* and anaerobes in the stools. These two populations had between $10^8$ and $10^9$ bacteria per gram per stool and rested stable throughout the entire duration of the treatment. Enterococci and Streptococci were present in the same proportions as that of the control. Treatment with R07 resulted in a 3 log decrease of Staphylococci. However this decrease was reversible 4 days after the end of treatment. Thus the quantity of Staphylococci at day 8 was the same as that at day 0.

The predominant species of the Enterobacteria in the R07 group was *Escherichia coli*, the predominant species of the Staphylococci was *Staphylococcus xylosus* and the species predominant for *Bacillus* was *Bacillus cereus*.

The encapsulated R07 nanocapsule at 20 mg/kg/day group had predominantly *Lactobacillus* and anaerobes in the stools. These two populations had between $10^8$ and $10^9$ bacteria per gram per stool and rested stable throughout the entire duration of the treatment. Enterobacteria, Enterococci and Streptococci were stable and had between $10^5$ and $10^6$ bacteria per gram per stool throughout the treatment. Staphylococci and *Bacillus* that formed part of the associated flora fluctuated as observed in the control group.

The predominant species of the Enterobacteria in the encapsulated R07 nanocapsule group was *Escherichia coli*, the predominant species of the Staphylococci was *Staphylococcus xylosus* and the species predominant for *Bacillus* was *Bacillus cereus*.

The encapsulated R07 nanocapsule at 40 mg/kg/day group was composed of mainly *Lactobacillus* and anaerobic bacteria that rested stable during the course of treatment, like observed with the control group. *Staphylococcus aureus* decreased 4 logs at day 2 and increased to 3.5 logs at day 3.

The predominant species of the Enterobacteria in the encapsulated R07 nanocapsule group was *Escherichia coli*, the predominant species of the Staphylococci was *Staphylococcus xylosus* and the species predominant for *Bacillus* was *Bacillus cereus*.

The empty nanocapsules at 40 mg/kg/day had predominantly *Lactobacillus* and anaerobes in the stools. These two populations had between $10^8$ and $10^9$ bacteria per gram per stool. Enterococci and Streptococci were present in proportions similar to the control. Staphylococci and *Bacillus* being part of the associated flora fluctuated.

The predominant species of the Enterobacteria in the empty nanocapsule group was *Escherichia coli*, the predominant species of the Staphylococci was *Staphylococcus xylosus* and the species predominant for *Bacillus* was *Bacillus cereus*.

The amoxicillin and clavulanic acid (AMC) had predominantly anaerobic bacteria quantified at $10^9$ bacteria per gram per stool. The *Lactobacillus* decreased 7 logs in the course of the treatment with AMC and this inoculated bacteria came back to a value of 6 logs a day 8, hence 4 days after the treatment was stopped. An augmentation of near 3 logs was observed with Enterobacteria and a decrease of 1 log was observed 4 days after treatment. For Enterococci and Streptococci an augmentation of 2 logs was observed and returned to normal after the treatment was stopped.

The predominant species of the Enterobacteria in the AMC (Augmentin) group was *Escherichia coli* up until day 3, then *Enterobacter cloacae*. The predominant species of the Staphylococci was *Staphylococcus xylosus* and the species predominant for *Bacillus* was *Bacillus cereus*.

The R07 at 20 mg/kg/day and fructo-oligosaccharide (FOS) group had *Escherichia coli* as the predominant species of the Enterobacteria, the predominant species of the Staphylococci was *Staphylococcus xylosus* and the species predominant for *Bacillus* was *Bacillus cereus*.

The encapsulated R07 nanocapsules group at 20 mg/kg/day and fructo-oligosaccharide group had *Lactobacillus* and anaerobic bacteria higher than 109 bacteria per gram per stool. Enterobacteria, Enterococci and Streptococci were stable through the course of the treatment.

The predominant species of the Enterobacteria in the encapsulated R07 nancapsule group was *Escherichia coli*, the predominant species of the Staphylococci was *Staphylococcus xylosus* and the species predominant for *Bacillus* was *Bacillus cereus*.

The encapsulated R07 nanocapsules group at 40 mg/kg/day and fructo-oligosaccharide group had Enterobacteria, which diminished 1.5 logs on day 2, which increased to normal on day 4 before finishing the treatment.

The predominant species of the Enterobacteria in the empty nanocapsule group was *Escherichia coli*, the predominant species of the Staphylococci was *Staphylococcus xylosus* and the species predominant for *Bacillus* was *Bacillus cereus*.

As can be seen from the above, the formulations of encapsulated R07 nanocapsules at 20 mg, encapsulated R07 nanocapsules at 40 mg, encapsulated R07 nanocapsules and fructo-oligosaccharides at 20 mg and encapsulated R07 nanocapsules at 40 mg and fructo-oliogosaccharides do not have any significant effect on the digestive commensal flora in mice. In contrast the administration of amoxicillin and clavulanic acid perturbed the flora by modifying the distribution of species of Enterobacteria in which *Enterobacter* replaced *Escherichia coli*.

Example 12

Measuring Zeta Potential

The zeta potential corresponds to a an electrokinetic measurement that is used to evaluate the colloidal behavior of an object in an aqueous solution. Thus Zeta potenetial is a physical property which is exhibited by any particle in suspension.

This parameter was measured. In general a very negative value or positive value of, for example −30 mV or +30 mV, indicates the presence of electokinetic charges on the surface of the bacteria or nanocapsule. A value in the interval, for example, of −5 mV or +5 mV, indicates a surface that is neutral with some electric dipoles without an electric charge are being produced by the particles.

Measurement was taken using empty nanocapsules alone, nanocapsules encapsulated with R07, various bacterial strains alone, various bacterial strains incubated with the empty capsules or various bacterial strains incubated with the encapsulated R07 nanocapsules via electrophoresis.

The empty nanocapsules were prepared according to Example 1.

The encapsulated R07 nanocapsules were prepared according to Example 2.

| Zeta Potential (mV) | Empty nanocapsules | R07 encapsulated | E. coli | P. aeruginosa | A. baumannii CIP | A. baumannii mucoid | A. baumannii non-mucoid |
|---|---|---|---|---|---|---|---|
| Alone | −7.58 ± 1 | −5.59 ± 1 | −35.97 ± 0.15 | −28.77 ± 0.42 | −25.13 ± 2 | −27.07 ± 3 | −30.03 ± 3 |
| Bacteria + empty nanocapsule | | | −10.38 ± 2 | −10.31 ± 2 | −11.23 ± 1 | −11.07 ± 1 | −12.97 ± 3 |
| Bacteria + encapsulated nanocapsule | | | −9.65 ± 1 | −7.32 ± 1 | −8.59 ± 1 | −2.63 ± 1 | −7.30 ± 1 |

The above results indicate that the empty nanocapsules or those nanocapsules encapsulated with R07 have similar values, which are negative and close to having a neutral surface. In contrast the different bacteria have very negative values thus having a very negative surface charge, which conforms to their structure of having bacterial shells.

In the case where the bacterial strains were incubated with the empty nanocapsules, there is a drop in voltage compared to the control. The zeta potential was around −30 mV prior to incubation with the empty nanocapsules and around −10 mV after incubation with the nanocapsules. Only a single peak corresponding to the bacterial strain was observed and not two corresponding to the bacterial strain and other empty nanocapsules in the aqueous suspension.

A still further decrease in voltage was observed when the bacterial strains were incubated with nanocapsules encapsulated with R07.

From the above results it can be concluded that the surface property of bacterial strains are modified when they are contacted with either empty nanocapsules or nanocapsules encapsulated with R07. The absence of a second peak when the nanocapsules were mixed with the various bacterial strains is an indication that the nanocapsules form a film that covers the surface of the bacteria.

The results with R07 show that the surface of the bacteria is modified and with *Acinetobacter baumannii* mucoid and *Acinetobacter. baumannii* mucoid the results are more profound. This bacteria is known to be antibiotic resistant and to form biofilms, which confer resistance to antimicrobial compounds (Gaddy et al *Future Microbiol.* 2009; 4:273-278).

Thus the present invention with either the empty nanocapsules or the encapsulated R07 nanocapsules can be used to inhibit cell density-dependant signaling as demonstrated in both gram positive and gram negative bacteria by quorum sensing. Therefore not only can the empty nanocapsules or encapsulated R07 nanocapsules may hinder the growth of bacteria but also may prevent the production of virulence factors and/or growth in biofilm communities.

Example 13

Resistance of SARM *S. aureus* ATCC25923 and Rifampicin to R07

This experiment was performed to evaluate the in vitro emergence of resistance to SARM *S. aureus* ATCC25923 and rifampicin to R07. R07 has three essential oils from oregano from Morocco or the Balkans having about 33.20% or 70% carvacol (14.7 unit grams of carvacrol), an essential oil from clove leaves from Madagascar having 82.547% eugenol (70.6 unit grams of eugenol) and essential oil from cinnamon from China having 77.57% of trans cinnamaldehyde (14.7 unit grams of trans cinnamaldehyde).

600 mg of rifampicine (Rifadine® Sanofi Aventis Lot A0360) and 1 g/ml R07 was diluted in DMSO at 60%. Mueller Hinton Agar was used in a standardized disk diffusion procedure for determining the susceptibility of rapidly growing aerobic microorganisms to antimicrobial agents. The SARM *S. aureus* ATCC25923 was streaked onto the plates to give counts equal to 0.5 McFarland standard of approximately 1.5 log 8 cfu/ml.

R07 and rifampicin concentration were introduced in the medium in order to obtain subminimal inhibitory concentration of the product in the medium. The test to evaluate the increase in resistance was carried out with a concentration of the product of two times the Minimal Inhibitory Concentration (MIC). The results are set forth in Table VII:

TABLE VII

| Minimal Inhibitory Concentration | *Staphlococcus aureus* |
|---|---|
| R07 | 0.10% |
| Minimal inhibitory concentration/4 of R07 | 0.03# |
| 2 times the minimal inhibitory concentration of R07 | 0.20% |
| Minimal inhibitory concentration of rifampicin | 0.008 mg/l |
| Minimal inhibitory concentration/4 of rifampicin | 0.002 mg/l |
| 2 times the minimal inhibitory concentration of rifampicin | 0.16 mg/l |

The appearance of resistance of *Staphylococcus aureus* with rifampicin was observed at the $6^{th}$ passage. A 0.38 ml/I inhibitory activity reappeared with rifampicin; thus, 47.5 times the initial minimal inhibitory concentration.

At 30 passages no resistance of *Staphylococcus aureus* was observed with R07.

Example 14

The Minimal Inhibitory Concentration of R07 Using Different Microorganisms

The minimal inhibitory concentration of R07 having three essential oils from oregano from Morocco or the Balkans having about 33.20% or 70% carvacol (14.7 unit grams of carvacrol), an essential oil from clove leaves from Madagascar having 82.57% eugenol (70.6 unit grams of eugenol) and essential oil from cinnamon from China having 77.57% of trans cinnamaldehyde (14.7 unit grams of trans cinnamaldehyde) and AT110 having four essential oils from about 11.86% carvacrol (5.25 unit grams of carvacrol), an essential oil from clove leaves from Madagascar having 63.28% eugenol (54.10 unit grams of eugenol) and essential oil from cinnamon from China having 13.56% of trans cinnamaldehyde (2.57 unit grams of trans cinnamaldehyde) and 11.3% trans-R-coryophyllene (1.8 unit grams of trans-β-caryophyllene) were determined for several bacterial microorganisms considered to be of medical interest.

The essential oils were also tested individually for their minimal inhibitory concentration.

Each solution was reconstituted in DMSO since the essential oils did not dissolve in water. The solution was first prepared at 40% in DMSO before being placed on the Muller-Hinton agar in the following manner in Table VIII:

TABLE VIII

| Final concentration in the composition in 20 ml of Muller-Hinton (mg/ml) | quantity of essential oils (µl) | quantity of water (µl) | quantity of Muller-Hinton (ml) |
|---|---|---|---|
| 0.5 | 25 | 0 | 20 |
| 0.75 | 37.5 | 0 | 20 |
| 1 | 50 | 0 | 20 |
| 1.5 | 75 | 0 | 20 |

TABLE VIII-continued

| Final concentration in the composition in 20 ml of Muller-Hinton (mg/ml) | quantity of essential oils (µl) | quantity of water (µl) | quantity of Muller-Hinton (ml) |
|---|---|---|---|
| 2 | 100 | 0 | 20 |
| 2.5 | 125 | 0 | 20 |
| 3 | 150 | 0 | 20 |
| 4 | 200 | 800 | 19 |
| 5 | 250 | 750 | 19 |
| 7.5 | 375 | 625 | 19 |
| 10 | 500 | 500 | 19 |
| 20 | 1,000 | 0 | 19 |

Twenty-two different microorganisms were tested and their minimal inhibitory concentration was tested. The results are set forth in the Table below:

TABLE VIII

| | Minimal Inhibitory Concentration in mg/ml | | | | | | | | | |
|---|---|---|---|---|---|---|---|---|---|---|
| microorganism | eugenol 63.28% | eugenol 63.28% | carvacrol 11.86% | carvacrol 11.68% | trans cinnamaldehyde 13.56% | trans cinnamaldehyde 13.56% | R07 | R07 | AT110 | AT110 |
| A. baumanni RCH | 0.75 | 1 | 1 | 1 | 0.75 | 2 | 0.75 | 0.75 | 0.5 | 0.75 |
| A. baumanni SAN008 | 0.75 | 1.5 | 1 | 1.5 | 1 | 2 | 0.75 | 0.75 | 0.5 | 0.75 |
| A. baumanni 12 | 1 | 1.5 | 1.5 | 1.5 | 1 | 1 | 0.75 | 0.75 | 0.75 | 0.75 |
| A. baumanni AYE | 0.75 | 1 | 1 | 1.5 | 1 | 2 | 0.75 | 0.75 | 0.5 | 0.75 |
| A. baumanni CIP7034 | 1 | 1.5 | 1 | 1.5 | 1 | 1 | 0.75 | 0.75 | 0.5 | 0.75 |
| A. baumanni CIP107292 | 1 | 1 | 1 | 1.5 | 0.75 | 2 | 0.75 | 0.75 | 0.5 | 0.75 |
| A. baumanni CIP5377 | 0.5 | 1 | 1 | 1 | 0.75 | 2 | 0.75 | 0.5 | 0.5 | 0.5 |
| S. aureus ATC25923 | 0.75 | 1.5 | 1.5 | 0.75 | 0.75 | 1.5 | 0.75 | 0.75 | 0.5 | 1 |
| S. aureus 0706C0025 | 1 | 1 | 1.5 | 2 | 0.75 | 0.5 | 0.75 | 0.75 | 0.75 | 1 |
| S. aureus 0702E0196 | 1 | 1.5 | 1.5 | 1 | 1 | 1.5 | 0.75 | 1 | 0.1 | 1 |
| S. aureus 0703H0036 | 1 | 1.5 | 1.5 | 2 | 0.75 | 1.5 | 0.75 | 0.75 | 0.75 | 1 |
| S. aureus 0701A0095 | 0.75 | 1.5 | 1.5 | 1.5 | 0.75 | 1.5 | 0.75 | 0.75 | 0.75 | 1 |
| E. coli ATCC25922 | 0.75 | 1.5 | 1.5 | 2 | 0.75 | 2 | 0.75 | 0.75 | 0.75 | 1 |
| E. coli 0705A0434 | 1 | 1.5 | 1.5 | 2 | 1 | 2 | 1 | 1 | 0.75 | 1 |
| E. cloacae 0705A1743 | 1 | 1.5 | 1.5 | 2 | 0.75 | 2 | 1 | 0.75 | 0 | 1 |
| E. aerogenes 0705A0867 | 1 | 1.5 | 1.5 | 2 | 1 | 2 | 0.75 | 0.75 | 75 | 1 |
| K. oxyloca 0705C0187 | 1 | 1.5 | 1.5 | 2 | 1 | 2 | 1 | 1 | 0.75 | 1 |
| Salmonell enteritidis 4 | 1 | 1.5 | 2 | 2.5 | 1 | 2 | 1 | 1 | 0.75 | 1 |
| P. aeroginosa ATCC27853 | 7.5 | 7.5 | 7.5 | 7.5 | 2 | 7.5 | 2.5 | 2 | 1.5 | 2 |
| P. aeroginosa 0704C0134 | 1.5 | 2 | 2.5 | 5 | 1 | 2 | 1.5 | 1.5 | 0.75 | 1.5 |
| P. aeroginosa 0703C0259 | 2.5 | 5 | 3 | 7.5 | 1.5 | 2 | 1.5 | 1.5 | 1 | 1.5 |

This Table illustrates that the essential oils when used alone have a higher minimal inhibitory concentration than compared with the combined essential oils of R07 and AT110. The mean inhibitory concentration of the essential oils when used alone is five times higher, having a mean concentration of 1 to 2 mg/ml compared when the essential oils were mixed together such as those formulated in R07 and AT110 which had a mean minimal inhibitory concentration of 0.76 mg/ml.

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the claims, including equivalents thereof.

Having described the invention, the following is claimed:

1. A composition comprising at least one essential oil or essential oil extract having a broad spectrum antibacterial activity, antiparasitic activity, antifungal activity, undesirable vegetation activity, weed activity and/or plant antipathogenic activity, wherein:
   a. said essential oil or essential oil extract is encapsulated within nanoparticles or lipidic nanocapsules obtained by a phase-inversion temperature method, whereby lipidic nanocapsules have an oily core of medium-chain triglycerides surrounded by a membrane made of lecithin and a PEGylated surfactant, and nanoparticles have a membrane made of lecithin and a PEGylated surfactant and no medium-chain triglycerides oily core, and
   b. said essential oil or essential oil extract is selected from the group of: essential oil from oregano, essential oil or essential oil extract from thyme, essential oil or essential oil extract from cloves, essential oil or essential oil extract from savory, essential oil or essential oil extract from ravintsara, essential oil or essential oil extract from laurel leaves, essential oil or essential oil extract from scotch pine, essential oil or essential oil extract from eucalyptus, essential oil or essential oil extract from paper bark, essential oil or essential oil extract from cinnamon and mixtures thereof.

2. The composition according to claim 1, further comprising at least one antibiotic that is either encapsulated within nanoparticles or lipidic nanocapsules along with the at least one essential oil or essential oil extract, or found in the composition in association with at least one essential oil or essential oil extract encapsulated within nanoparticles or lipidic nanocapsules, wherein said at least one antibiotic is selected from the group of a beta-lactamine antibiotic, amoxicilline, clavulanic acid, piperacilline which can be associated or not with tazobactam, cloxacillin, cefuroxime, cefotaxime or impenem, an aminoside antibiotic, gentamicin or amikacin, a fluroquinolone antibiotic, ciprofloxacin or ofloxacin, a fosfomycine antibiotic, a glycopeptide antibiotic, vancomycin or teicoplanin, a nitrofuran antibiotic, a rifamycin antibiotic, a macrolide antibiotic, josamycin or clarithromycin, a nitro-imidazole antibiotic, a sulfamide, a trimethoprim antibiotic, a synergistin antibiotic, their pharmaceutically acceptable salts and mixtures thereof.

3. The composition according to claim 1, wherein at least one essential oil is selected from the group of: essential oil from oregano from Spain or Morocco or the Balkans, essential oil or essential oil extract from the leaves of cloves, essential oil or essential oil extract from green paper bark, essential oil or essential oil extract from red thyme, essential oil or essential oil extract from Chinese cinnamon and mixtures thereof.

4. The composition according to claim 1, wherein the essential oils or essential oil extracts comprise or consist of:
   about 5 to about 40% by weight, or about 20% to about 30% by weight, or about 25% by weight, of essential oil or essential oil extract from oregano; and/or
   about 1% to about 25% by weight, or about 3% to about 14% by weight, or about 9% by weight, of essential oil or essential oil extract from thyme; and/or
   about 1% to 75% by weight, or about 70% by weight, of essential oil or essential oil extract from cloves; and/or
   about 1% to 20% by weight, or about 1% to about 12% by weight, or about 6% by weight, of essential oil or essential oil extract from savory; and/or
   about 1% to 20% by weight, or about 4% to about 15% by weight, or about 9% by weight, of essential oil or essential oil extract from ravintsara; and/or
   about 1% to 20% by weight, or about 4% to about 15% by weight, or about 9% by weight, of essential oil or essential oil extract from laurel leaves; and/or
   about 1% to 20% by weight, or about 1% to about 12% by weight, or about 6% by weight, of essential oil or essential oil extract from scotch pine; and/or
   about 1% to 20% by weight, or about 1% to about 12% by weight, or about 6% by weight, of essential oil or essential oil extract from paper bark; and/or
   about 1% to 30% by weight, or about 1% to about 15% by weight, or about 15% by weight, of essential oil or essential oil extract from cinnamon.

5. The composition according to claim 1, comprising about 15% by weight of an essential oil from oregano, about 70% by weight of an essential oil from clove and about 15% by weight of essential oil from cinnamon and optionally at least one antibiotic that is encapsulated or associated with the at least one essential oil or comprising of about 63.28% of an essential oil extract from clove or clove leaves, 11.86% of essential oil extract from cinnamon, 13.56% of an essential oil extract from cinnamon bark and 11.3% of an essential oil extract from oregano, cloves and/or cinnamon.

6. The composition according to claim 1, comprising an essential oil from oregano from Morocco or the Balkans having about 33.20% or 70% of carvacrol (14.7 unit grams of carvacrol), an essential oil from clove leaves or cloves from Madagascar having 82.57% eugenol (70.6 unit grams of eugenol) and essential oil from cinnamon from China having 77.57% of trans cinnamaldehyde (14.7 unit grams of trans cinnamaldehyde).

7. The composition according to claim 1, having four essential oil extracts, which are about 11.86% carvacrol extract (5.25 unit grams of carvacrol) from oregano, 63.28% eugenol (54.10 unit grams of eugenol) an essential oil extract from clove leaves or cloves from Madagascar, 13.56% of trans cinnamaldehyde extract (2.57 unit grams of trans cinnamaldehyde) an essential oil extract from cinnamon from China and 11.3% trans-β-caryophyllene (1.80 unit grams of trans-β-caryophyllene) from oregano, cloves and/ or cinnamon.

8. The composition according to claim 1, wherein the nanoparticle has a size of between 1 nm and 100 nm and wherein 100 µl to 500 µl of said essential oil(s) is encapsulated or the lipidic nanocapsule has a size of between 20 nm and 200 nm and wherein 100 µl to 500 µl of said essential oil(s) is encapsulated.

9. The composition according to claim 1, wherein each of the at least one essential oil(s) or at least one essential oil extract present in said composition is encapsulated at a concentration ranging from 0.01% to 2% by weight, 0.05% to 0.5% by weight, 0.05% to 1% by weight, 0.5% to 80% by weight or 0.2% to 25% by weight.

10. The composition according to claim 1, wherein the lipidic nanocapsule comprises a mixture of soybean lecithin at 69% of phosphatidylcholine, caprylic-capric acid triglycerides and a mixture of free polyethylene glycol 660 and polyethylene glycol 66-hydroxystearate.

11. The composition according to claim 1, further comprising a pharmaceutically acceptable carrier that is saline or buffered saline, and/or the composition is further formulated to be administered as a medicament.

* * * * *